United States Patent
Göppel et al.

(10) Patent No.: US 7,341,712 B2
(45) Date of Patent: Mar. 11, 2008

(54) COSMETIC OR DERMATOLOGICAL LIGHT-PROTECTIVE FORMULATION COMPRISING A HYDROXYBENZOPHENONE AND A BENZOXAZOLE DERIVATIVE

(75) Inventors: Anja Göppel, Hamburg (DE); Jens Schulz, Schenefeld (DE); Anja Eitrich, Hamburg (DE)

(73) Assignee: Beiersdorf AG, Hamburg (DE)

( * ) Notice: Subject to any disclaimer, the term of this patent is extended or adjusted under 35 U.S.C. 154(b) by 664 days.

(21) Appl. No.: 10/871,861

(22) Filed: Jun. 18, 2004

(65) Prior Publication Data

US 2005/0031556 A1    Feb. 10, 2005

Related U.S. Application Data

(63) Continuation of application No. PCT/EP02/14391, filed on Dec. 17, 2002.

(30) Foreign Application Priority Data

Dec. 20, 2001   (DE) ............... 101 62 843
Oct. 23, 2002   (DE) ............... 102 49 367

(51) Int. Cl.
  A61Q 17/04   (2006.01)
  A61Q 17/00   (2006.01)
  A61Q 19/04   (2006.01)
  A61Q 19/00   (2006.01)
  A61K 8/02    (2006.01)

(52) U.S. Cl. .................. 424/59; 424/60; 424/400; 424/401

(58) Field of Classification Search .......... 424/59, 424/60, 400, 401
See application file for complete search history.

(56) References Cited

U.S. PATENT DOCUMENTS

| 4,076,687 A | 2/1978 | Irick, Jr. et al. |
| 4,250,315 A | 2/1981 | Poncioni |
| 4,668,505 A | 5/1987 | Grollier et al. |
| 5,154,850 A | 10/1992 | Deguchi et al. |
| 5,302,376 A | 4/1994 | Forestier et al. |
| 5,585,091 A | 12/1996 | Pelzer et al. |
| 5,744,127 A | 4/1998 | Giuseppe et al. |
| 5,955,060 A | 9/1999 | Huglin et al. |
| 5,961,960 A | 10/1999 | Dilk et al. |
| 6,214,324 B1 | 4/2001 | Candau |
| 6,248,311 B1* | 6/2001 | Candau .................. 424/59 |
| 6,251,373 B1 | 6/2001 | Candau |
| 6,296,835 B1 | 10/2001 | Candau |
| 6,409,995 B1* | 6/2002 | Habeck et al. ......... 424/59 |
| 6,458,342 B1 | 10/2002 | Heidenfelder et al. |
| 6,514,485 B1 | 2/2003 | Malpede et al. |
| 2001/0053856 A1 | 12/2001 | Leduc et al. |
| 2002/0001570 A1 | 1/2002 | Heidenfelder et al. |
| 2002/0085981 A1 | 7/2002 | Raspantii et al. |

FOREIGN PATENT DOCUMENTS

| DE | 100 63 867 A1 | 7/2002 |
| EP | 0 832 641 A2 | 4/1998 |
| EP | 1 142 552 A2 | 10/2001 |
| FR | 2 779 957 | 12/1999 |
| WO | WO 01/49686 A1 | 7/2001 |

OTHER PUBLICATIONS

Search Report from German Application No. 101 62 844.7, dated Aug. 29, 2002.
Search Report from German Application No. 101 62 842.0, dated Aug. 29, 2002.
Search Report from German Application No. 101 62, 843.9, dated Aug. 16, 2002.
Search Report from corresponding German Application No. 102 49 367.7, dated Apr. 1, 2003.
Search Report from German Application No. 101 62 841.2, dated Aug. 28, 2002.
International Search Report from corresponding International Application No. PCT/EP02/14391 dated Mar. 21, 2003.

* cited by examiner

Primary Examiner—Shelley A. Dodson
(74) Attorney, Agent, or Firm—Greenblum & Bernstein, P.L.C.

(57) ABSTRACT

The invention is a light-protective cosmetic or dermatological preparation, comprising (a) at least hydroxybenzophenone and (b) at least one benzoxazole derivative. The invention is also a cosmetic or dermatological preparation comprising at least one hydroxybenzophenone of a specified chemical structure and at least one benzoxazole derivative. The invention is also a method of treating or preventing cosmetic or dermatological changes in the skin, a method of tanning or accelerating tanning of the skin, and a method of protecting the skin against light-induced aging, each comprising applying the preparation to the skin. The invention also includes a wipe impregnated with the preparation.

50 Claims, No Drawings

COSMETIC OR DERMATOLOGICAL LIGHT-PROTECTIVE FORMULATION COMPRISING A HYDROXYBENZOPHENONE AND A BENZOXAZOLE DERIVATIVE

CROSS-REFERENCE TO RELATED APPLICATIONS

This is a continuation application of PCT/EP02/14391, filed Dec. 17, 2002, which is incorporated herein by reference in its entirety, and also claims the benefit of German Priority Application No. 101 62 843.9, filed Dec. 20, 2001 and 102 49 367.7, filed Oct. 23, 2002.

FIELD OF THE INVENTION

The present invention relates to cosmetic and dermatological light-protective preparations, in particular it relates to cosmetic and dermatological formulations with increased UV-A protection performance.

BACKGROUND OF THE INVENTION

The harmful effect of the ultraviolet part of solar radiation on the skin is generally known. Depending on their particular wavelength, the rays have different effects on the skin as an organ:

The so-called UV-C radiation with a wavelength between 100 and 280 nm is absorbed by the ozone layer in the Earth's atmosphere and accordingly is not found in the solar spectrum. It is therefore of no physiological importance during sunbathing.

The so-called UV-B region is between 290 nm and 320 nm. UV-B rays are essentially responsible for the long-lasting tanning of the skin, but can at the same time cause an erythema, simple sunburn or even burns of greater or lesser severity. Chronic photodamage, photodermatoses and Herpes solaris can also be caused by UV-B radiation.

It has for a long time been incorrectly assumed that long-wave UV-A radiation with a wavelength between 320 nm and 400 nm only has a negligible biological effect and that, correspondingly, the UV-B rays are responsible for most photodamage to the human skin. However, in the meantime, numerous studies have studied that UV-A radiation is much more hazardous than UV-B radiation with regard to the triggering of photodynamic, specifically phototoxic reactions and chronic changes in the skin. The harmful influence of UV-B radiation can also be further intensified by UV-A radiation.

Thus, it has, inter alia, been found that even UV-A radiation suffices under very normal everyday conditions to harm, within a short time, the collagen and elastin fibers which are of essential importance for the structure and strength of the skin. The consequences are chronic photo-induced changes in the skin—the skin "ages" prematurely. The clinical appearance of skin aged by light includes, for example, wrinkles and lines, and also an irregular, furrowed relief. In addition, the parts affected by photo-induced skin aging have irregular pigmentation. The formation of brown spots, keratoses and even carcinomas or malignant melanomas is also possible. Skin aged prematurely by everyday UV exposure is, moreover, characterized by lower activity of the Langerhans cells and slight, chronic inflammation.

Approximately 90% of the ultraviolet radiation which reaches the Earth consists of UV-A rays. While UV-B radiation varies widely depending on numerous factors (e.g. time of year and time of day or degree of latitude), UV-A radiation remains relatively constant day to day irrespective of the time of year and time of day or geographical factors. At the same time, the majority of UV-A radiation penetrates into the living epidermis, while approximately 70% of UV-B rays are retained by the horny layer.

The relatively recent findings concerning the effect of UV-A rays on the skin have led to increased attention now being devoted to protective measures for this ray range. In practice, no sunscreen product is complete any more without an effective UV-A filter effect, and pure UV-B filter preparations are rare.

When applying a sunscreen to the skin, the ultraviolet rays can be weakened through two effects: firstly, by reflection and scattering of the rays at the surface of pulverulent solids (physical light-protective) and, secondly, by absorption on chemical substances (chemical light-protective). Depending on which wavelength region is absorbed, a distinction is made between UV-B filters (absorption range 280 to 320 nm), UV-A filters (absorption range 320 to 400 nm) and broadband filters (absorption range 290 to about 380 nm).

To protect against UV-B radiation, numerous compounds are known, the absorption maximum of which should be around 308 nm as far as possible since this is the highest erythema effectiveness of solar radiation. Typical UV-B filters are, for example, derivatives of 3-benzylidenecamphor, of 4-aminobenzoic acid, of cinnamic acid, of salicylic acid, of benzophenone, and also of 2-phenylbenzimidazole.

Some compounds are also known for protecting against UV-A radiation, such as, in particular, dibenzoylmethane derivatives. However, dibenzoylmethane derivatives are generally not photostable, as a result of which cosmetic or dermatological preparations with a content of this substance should also comprise certain UV stabilizers. Further known UV-A filter substances are certain water-soluble, sulfonated UV filter substances, such as, for example, phenylene-1,4-bis(2-benzimidazyl)-3,3'-5,5'-tetrasulfonic acid and its salts.

Besides the pure UV-A or UV-B filters, there are substances which cover both regions. This group of broadband filters includes, for example, asymmetrically substituted s-triazine compounds, such as, for example, 2,4-bis{[4-(2-ethylhexyloxy)-2-hydroxy]phenyl}-6-(4-methoxyphenyl)-1,3,5-triazine (INCI: BisEthylhexyloxyphenol Methoxyphenyl Triazine), certain benzophenones, such as, for example, 2-hydroxy-4-methoxybenzophenone (INCI: Benzophenone 3) or 2,2'-methylenebis(6-(2H-benzotriazole-2-yl)-4-(1,1,3,3-tetramethylbutyl)phenol) (INCI: Methylene Bis-Benzotriazolyl Tetramethylenebutylphenol).

In general, the light absorption behavior of light-protective filter substances is very well known and documented, especially as there are positive lists for the use of such substances in most industrialized countries, which impose very strict standards on the documentation. Since, in order to characterize a filter substance, not only is the position of the absorption maximum important, but primarily the absorption range, absorption spectra are recorded for each substance. However, the absorbance values can at best be a guide for the concentration of the substances in the finished formulations since interactions with ingredients of the skin or of the surface of the skin itself may give rise to imponderables. In addition, it is usually difficult to estimate beforehand how uniformly and thickly the filter substance is distributed in and on the horny layer of the skin.

To test the UV-A protection performance, use is usually made of the IPD method (IPD=immediate pigment darkening). Similarly to the determination of the sun protection factor, this method gives a value which indicates how much longer the skin protected with the light-protective composition can be irradiated with UV-A radiation until the pigmentation which occurs is the same as for the unprotected skin.

The use concentration of known light-protective filter substances present in the form of a solid, which exhibit a high filter effect in the UV-A region is, however, often limited—especially in combination with other substances to be dissolved. This therefore gives rise to certain technical difficulties relating to formulation in achieving relatively high sun protection factors or UV-A protection performance.

SUMMARY OF THE INVENTION

Since light-protective filter substances are generally expensive and since some light-protective filter substances are also difficult to incorporate into cosmetic or dermatological preparations in relatively high concentrations, it was an object of the invention to arrive, in a simple and cost-effective manner, at preparations which, despite having unusually low concentrations of conventional UV-A light-protective filter substances, nevertheless achieve an acceptable or even high UV-A protection performance.

It was surprising and could not have been foreseen by the person skilled in the art that light-protective cosmetic or dermatological preparations, characterized in that they comprise
(a) at least one hydroxybenzophenone and
(b) at least one benzoxazole derivative,
would overcome the disadvantages of the prior art.

The preparations according to the invention are entirely satisfactory preparations in every respect, which are not restricted to a limited choice of raw materials. Accordingly, they are particularly suitable as bases for preparations with diverse application purposes. The preparations according to the invention exhibit very good sensory and cosmetic properties, such as, for example, extensibility on the skin or the ability to be absorbed into the skin, and are further characterized by very good light-protective effectiveness, an exceptionally high UV-A protection performance, and by excellent skin compatibility coupled with excellent skincare data.

The invention therefore also provides light-protective cosmetic or dermatological preparations, characterized in that they comprise synergistic substance combinations of
(a) at least one hydroxybenzophenone and
(b) at least one benzoxazole derivative,
where the UV protection performance, in particular the UV-A protection performance, of these preparations is increased supraproportionally.

Surprisingly, the substance combinations according to the invention act synergistically, i.e. superadditively relative to the individual components. They are photostable without further additives and exhibit a surprisingly high protection performance in the UV-A region.

DETAILED DESCRIPTION OF THE PREFERRED EMBODIMENTS

For the purposes of the present invention, advantageous benzoxazole derivatives are characterized by the following structural formula,

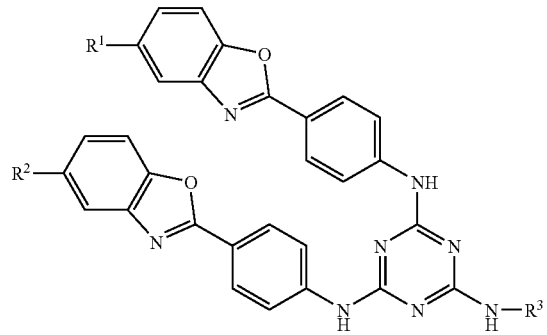

in which $R^1$, $R^2$ and $R^3$, independently of one another, are chosen from the group of branched or unbranched, saturated or unsaturated alkyl radicals having 1 to 10 carbon atoms. It is particularly advantageous according to the invention to choose the radicals $R^1$ and $R^2$ to be the same, in particular from the group of branched alkyl radicals having 3 to 5 carbon atoms. It is also particularly advantageous for the purposes of the present invention if $R^3$ is an unbranched or branched alkyl radical having 8 carbon atoms, in particular the 2-ethylhexyl radical.

A benzoxazole derivative which is particularly preferred according to the invention is 2,4-bis[5-1(dimethylpropyl)benzoxazole-2-yl-(4-phenyl)imino]-6-(2-ethylhexyl)imino-1,3,5-triazine with the CAS No. 288254-16-0, which is characterized by the structural formula

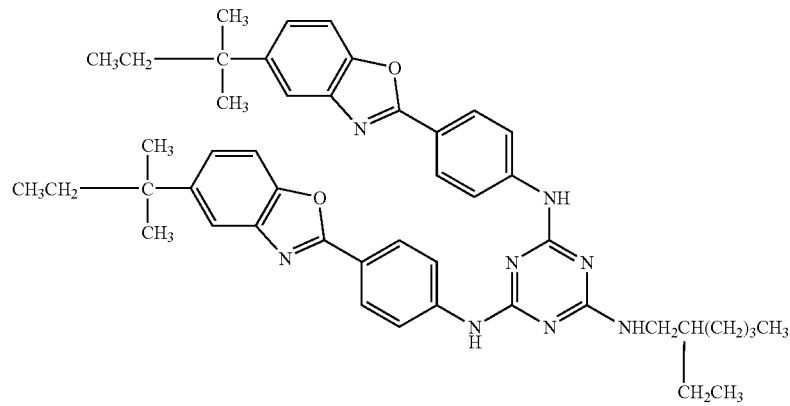

and is available from 3V Sigma under the trade name Uvasorb® K2A.

The benzoxazole derivative or derivatives are advantageously in dissolved form in the cosmetic preparations according to the invention. It may, however, also be advantageous in some circumstances if the benzoxazole derivative or derivatives are present in pigmentary, i.e. undissolved, form—for example in particle sizes of from 10 nm to 300 nm.

The total amount of one or more benzoxazole derivatives in the finished cosmetic or dermatological preparations is advantageously chosen from the range from 0.01% by weight to 20% by weight, preferably from 0.1 to 10% by weight, in each case based on the total weight of the preparations.

Hydroxybenzophenones are characterized by the following structural formula:

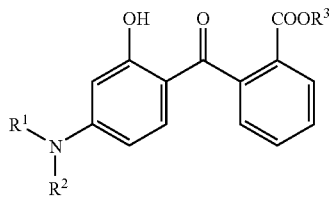

in which
R$^1$ and R$^2$, independently of one another, are hydrogen, C$_1$-C$_{20}$-alkyl, C$_3$-C$_{10}$-cycloalkyl or C$_3$-C$_{10}$-cycloalkenyl, where the substituents R$^1$ and R$^2$, together with the nitrogen atom to which they are bonded, can form a 5-membered or 6-membered ring and
R$^3$ is a C$_1$-C$_{20}$-alkyl radical.

A particularly advantageous hydroxybenzophenone for the purposes of the present invention is hexyl 2-(4'-diethylamino-2'-hydroxybenzoyl)benzoate (also: aminobenzophenone), which is characterized by the following structure:

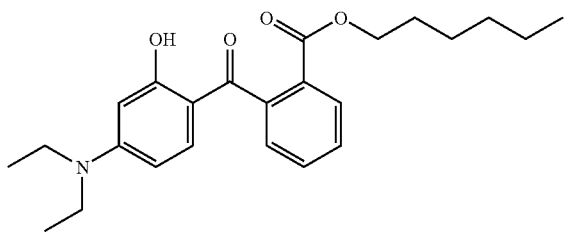

and is available under the Uvinul A Plus from BASF.

The total amount of one or more hydroxybenzophenones in the finished cosmetic or dermatological preparations is advantageously chosen from the range 0.01% by weight to 20% by weight, preferably from 0.1 to 10% by weight, in each case based on the total weight of the preparations.

It is particularly advantageous to choose the weight ratios of the benzoxazole derivative or derivatives to the hydroxybenzophenone or hydroxybenzophenones as 30:1 to 1:30, preferably as 10:1 to 1:10, particularly preferably as 5:1 to 1:5.

Besides comprising one or more oil phases, the preparations for the purposes of the present invention may preferably additionally comprise one or more water phases and be present, for example, in the form of W/O, O/W W/O/W or O/W/O emulsions. Such formulations can preferably also be microemulsions, sticks, mousses, solids emulsions (i.e. emulsions which are stabilized by solids, e.g. Pickering emulsions), sprayable emulsions or hydrodispersions. Furthermore, the preparations may advantageously also be oil-free or aqueous/alcoholic solutions.

Sprayable Emulsions, in Particular Microemulsions

For the purposes of the present invention, sprayable O/W emulsions, in particular O/W microemulsions, are particularly advantageous.

The droplet diameters of the customary "simple", i.e. non-multiple, emulsions are in the range from about 1 µm to about 50 µm. Such "macroemulsions" are, without further coloring additives, multi-white in color and opaque. Finer "macroemulsions", the droplet diameters of which are in the range from about 0.5 µm to about 1 µm, are, again without coloring additives, bluish-white in color and opaque. Such "macroemulsions" usually have a high viscosity.

The droplet diameter of microemulsions for the purposes of the present invention, by contrast, is in the range from about 50 to about 500 nm. Such microemulsions are bluish-white in color to translucent and in most cases of low viscosity. The viscosity of many microemulsions of the O/W type is comparable with that of water.

An advantage of microemulsions is that active ingredients can be present in an essentially more finely disperse form in the disperse phase than in the disperse phase of "macroemulsions". A further advantage is that, due to their low viscosity, they are sprayable. If microemulsions are used as cosmetics, corresponding products are characterized by high cosmetic elegance.

Advantageous according to the invention are, in particular, O/W microemulsions which are obtainable using the so-called phase-inversion temperature technology and comprise at least one emulsifier (emulsifier A), which is chosen from the group of emulsifiers with the following properties:
their lipophilicity is dependent on the temperature, such that by increasing the temperature the lipophilicity increases, and by reducing the temperature the lipophilicity of the emulsifier decreases.

Advantageous emulsifiers A are, for example, polyethoxylated fatty acids (PEG-100 stearate, PEG-20 stearate, PEG-150 laurath, PEG-8 distearate and the like), polyethoxylated fatty alcohols (cetearath-12, cetearath-20, isoceteth-20, beheneth-20, laureth-9 etc.), and alkyl polyglycosides (cetearyl glycoside, stearyl glycoside, palmityl glycoside etc.).

If the phase inversion is triggered essentially by varying the temperature, O/W emulsions, in particular O/W microemulsions, are obtainable where the size of the oil droplets is determined essentially by the concentration of the emulsifier or the emulsifiers used, in such a way that a higher emulsifier concentration results in relatively small droplets, and a lower emulsifier concentration results in relatively large droplets. The droplet sizes are usually between 20 and 500 nm.

For the purposes of the present invention, it is in some instances advantageous to use further W/O or O/W emulsifiers which do not fall under the definition of emulsifer A, for example in order to increase the water resistance of the preparations according to the invention. For example, alkylmethicone copolyols or alkyldimethicone copolyols (in particular cetyl dimethicone copolyol, lauryl methicone copolyol), W/O emulsifiers (such as, for example, sorbitan stearate, glyceryl stearate, glycerol stearate, sorbitan oleate, lecithin, glyceryl isostearate, polyglyceryl-3 oleate, polyglyceryl-3 diisostearate, PEG-7 hydrogenated castor oil, polyglyceryl-4 isostearate, acrylate/$C_{10-30}$-alkyl acrylate crosspolymer, sorbitan isostearate, poloxamer 101, polyglyceryl-2 dipolyhydroxy-stearate, polyglyceryl-3 diisostearate, polyglyceryl-4 dipolyhydroxystearate, PEG-30 dipolyhydroxystearate, diisostearoyl polyglyceryl-3 diisostearate, glycol distearate, polyglyceryl-3 dipolyhydroxystearate) or fatty acid esters of sulfuric acid or phosphoric acid (cetyl phosphate, trilaureth-4 phosphate, trioleth-8 phosphate, stearyl phosphate, cetearyl sulfate etc.) can be used.

Further advantageous sprayable O/W emulsions for the purposes of the present invention are low-viscosity cosmetic or dermatological hydrodispersions which comprise at least one oil phase and at least one water phase, where the preparation is stabilized by at least one gel former and does not necessarily have to comprise emulsifiers, but may comprise one or more emulsifiers.

Advantageous gel formers for such preparations are, for example, copolymers of $C_{10-30}$-alkyl acrylates and one or more monomers of acrylic acid, of methacrylic acid or esters thereof. The INCI name for such compounds is "Acrylates/C10-30 Alkyl Acrylate Crosspolymer". The Pemulen® grades TR1, TR2 and TRZ from Goodrich (Noveon) are particularly advantageous.

Carbopols are also advantageous gel formers for such preparations. Carbopols are polymers of acrylic acid, in particular also acrylate-alkyl acrylate copolymers. Advantageous carbopols are, for example, the grades 907, 910, 934, 940, 941, 951, 954, 980, 981, 1342, 1382, 2984 and 5984, likewise the ETD grades 2020, 2050 and Carbopol Ultrez 10. Further advantageous gel formers for such preparations are xanthan gum, cellulose derivatives and carob seed flour.

Possible (optional) emulsifiers which may be used are ethoxylated fatty alcohols or ethoxylated fatty acids (in particular PEG-100 stearate, ceteareth-20) and other nonionic surface-active substances.

The very low-viscosity to sprayable emulsions may also advantageously be W/O emulsions or water-in-silicone oil (W/S) emulsions. W/O or W/S emulsions which comprise
 at least one silicone emulsifier (W/S) with a HLB value of $\leqq 8$ or at least one W/O emulsifier with a HLB value of <7 and
 at least one O/W emulsifier with a HLB value of >10 are particularly advantageous.

Such preparations further comprise at least 20% by weight of lipids, where the lipid phase can also advantageously comprise silicone oils, or even consist entirely of such oils.

The silicone emulsifier or emulsifiers can advantageously be chosen from the group of alkyl methicone copolyols and alkyldimethicone copolyols (e.g. dimethicone copolyols which are sold by Goldschmidt AG under the trade names Abil® B 8842, Abil® B 8843, Abil® B 8847, Abil® B 8851, Abil® B 8852, Abil® B 8863, Abil® B 8873 and Abil® B 88183, cetyl dimethicone copolyol [Goldschmidt AG/Abil® EM 90], cyclomethicone dimethicone copolyol [Goldschmidt AG/Abil® EM 97], lauryl methicone copolyol [Dow Corning Ltd./Dow Corning® 5200 Formulation Aid], octyl dimethicone ethoxyglucoside [Wacker].

The W/O emulsifier or emulsifiers with a HLB value of <7 can advantageously be chosen from the following group: sorbitan stearate, sorbitan oleate, lecithin, glyceryl lanolate, lanolin, hydrogenated castor oil, glyceryl isostearate, polyglyceryl-3 oleate, pentaerythrityl isostearate, methylglucose dioleate, methylglucose dioleate in a mixture with hydroxystearate and beeswax, PEG-7 hydrogenated castor oil, polyglyceryl-4 isostearate, hexyl laurate, acrylate/$C_{10-30}$-alkyl acrylate crosspolymer, sorbitan isostearate, poloxamer 101, polyglyceryl-2 dipolyhydroxystearate, polyglyceryl-3 diisostearate, PEG-30 dipolyhydroxystearate, diisostearoyl polyglyceryl-3 diisostearate, polyglyceryl-3 dipolyhydroxystearate, polyglyceryl-4 dipolyhydroxystearate, polyglyceryl-3 dioleate.

The O/W emulsifier or emulsifiers with a HLB value of >10 can advantageously be chosen from the following group: glyceryl stearate in a mixture with ceteareth-20, ceteareth-25, ceteareth-6 in a mixture with stearyl alcohol, cetylstearyl alcohol in a mixture with PEG40 castor oil and sodium cetylstearyl sulfate, triceteareth-4 phosphate, glyceryl stearate, sodium cetylstearyl sulfate, lecithin trilaureth-4 phosphate, laureth-4 phosphate, stearic acid, propylene glycol stearate SE, PEG-9 stearate, PEG-20 stearate, PEG-30 stearate, PEG40 stearate, PEG-100 stearate, ceteth-2, ceteth-20, polysorbate-20, polysorbate-60, polysorbate-65, polysorbate-100, glyceryl stearate in a mixture with PEG-100 stearate, ceteareth-3, isostearyl glyceryl ether, cetylstearyl alcohol in a mixture with sodium cetylstearyl sulfate, PEG-40 stearate, glycol distearate, PEG-22 dodecyl glycol copolymer, polyglyceryl-2 PEG-4 stearate, ceteareth-12, ceteareth-20, ceteareth-30, methylglucose sesquistearate, steareth-10, PEG-20 stearate, steareth-21, steareth-20, isosteareth-20, PEG-45/dodecyl glycol copolymer, methoxy-PEG-22/dodecyl glycol copolymer, glyceryl stearate SE, ceteth-20, PEG-20 methylglucose sesquistearate, glyceryl stearate citrate, cetyl phosphate, cetearyl sulfate, sorbitan sesquioleate, triceteareth4 phosphate, trilaureth4 phosphate, polyglyceryl methylglucose distearate, potassium cetyl phosphate, isosteareth-10, polyglyceryl-2 sesquiisostearate, ceteth-10, isoceteth-20, glyceryl stearate in a mixture with ceteareth-20, ceteareth-12, cetylstearyl alcohol and cetyl palmitate, PEG-30 stearate, PEG-40 stearate, PEG-100 stearate.

Aqueous-alcoholic solutions are also advantageous. They can comprise from 0% by weight to 90% by weight of ethanol. Aqueous-alcoholic solutions for the purposes of the present invention may advantageously also comprise solubility promoters, such as, for example, PEG40 or PEG-60 hydrogenated castor oil.

The preparations according to the invention can advantageously also be used as cosmetic or dermatological impregnation solutions with which water-insoluble substrates in particular—such as, for example, woven or nonwoven wipes—are moistened. Impregnation solutions of this type are preferably of low viscosity, in particular sprayable (such as, for example, PIT emulsions, hydrodispersions, W/O emulsions, oils (see below), aqueous solutions etc.) and preferably have a viscosity of less than 2000 mPa·s, in particular less than 1500 mPa·s (measuring device: Haake Viskotester VT-02 at 25° C.). They can be used to obtain, for example, cosmetic sunscreen wipes, care wipes and the like, which represent the combination of a soft, water-insoluble material with the low viscosity cosmetic and dermatological impregnation solution.

Oils

The preparations according to the invention can advantageously also be in the form of water-free oils or oil gels or pastes. Examples of advantageous oils are synthetic, semi-synthetic or natural oils such as, for example, rapeseed oil, rice oil, avocado oil, olive oil, mineral oil, cocoglycerides, butylene glycol dicaprylate/dicaprate, $C_{12-15}$ alkyl benzoate, dicaprylyl carbonate, octyldodecanol and the like. Oil gel formers which may be used are diverse waxes with a melting point >25° C. Also advantageous are gel formers from the group of Aerosils, of alkyl galactomannans (e.g. N-Hance AG 200 and N-Hance AG 50 from Hercules) and polyethylene derivatives.

Mousses

Also particularly advantageous for the purposes of the present invention are self-foaming, foam-like, after-foaming or foamable cosmetic and dermatological preparations.

"Self-foaming", "foam-like", "after-foaming" and "foamable" preparations are understood as meaning preparations from which foams can in principle be produced by introducing one or more gases—whether during the preparation process, whether upon use by the consumer or in another way. In such foams, the gas bubbles are (randomly) distributed in one (or more) liquid phase(s), where the (foamed) preparations do not necessarily have to have the appearance of a foam in macroscopic terms. Cosmetic or dermatological preparations (foamed) according to the invention (referred to below for the sake of simplicity also as foams) may, for example, be macroscopically visibly dispersed systems of gases dispersed in liquids. The foam character may, however, for example also only be visible under a (light) microscope. Moreover, foams according to the invention—particularly when the gas bubbles are too small to be seen under a light microscope—are also evident from the considerable volume increase of the system.

For the purposes of the present invention, such preparations advantageously comprise an emulsifier system which consists of A. at least one emulsifier chosen from the group of completely neutralized, partially neutralized or unneutralized, branched or unbranched, saturated or unsaturated fatty acids with a chain length of from 10 to 40 carbon atoms,
B. at least one emulsifier chosen from the group of polyethoxylated fatty acid esters with a chain length of from 10 to 40 carbon atoms and with a degree of ethoxylation of from 5 to 100 and
C. at least one coemulsifier C chosen from the group of saturated or unsaturated, branched or unbranched fatty alcohols with a chain length of from 10 to 40 carbon atoms.

The emulsifier or emulsifiers A are preferably chosen from the group of fatty acids, which are completely or partially neutralized with customary alkalis (such as, for example, sodium hydroxide or potassium hydroxide, sodium carbonate or potassium carbonate, and mono- or triethanolamine). Stearic acid and stearates, isostearic acid and isostearates, palmitic acid and palmitates, and myristic acid and myristates, for example, are particularly advantageous.

The emulsifier or emulsifiers B are preferably chosen from the following group: PEG-9 stearate, PEG-8 distearate, PEG-20 stearate, PEG-8 stearate, PEG-8 oleate, PEG-25 glyceryl trioleate, PEG-40 sorbitan lanolate, PEG-15 glyceryl ricinoleate, PEG-20 glyceryl stearate, PEG-20 glyceryl isostearate, PEG-20 glyceryl oleate, PEG-20 stearate, PEG-20 methylglucose sesquistearate, PEG-30 glyceryl isostearate, PEG-20 glyceryl laurate, PEG-30 stearate, PEG-30 glyceryl stearate, PEG40 stearate, PEG-30 glyceryl laurate, PEG-50 stearate, PEG-100 stearate, PEG-150 laurate. Polyethoxylated stearic esters, for example, are particularly advantageous.

According to the invention, the coemulsifier or the coemulsifiers C are preferably chosen from the following group: behenyl alcohol ($C_{22}H_{45}OH$), cetearyl alcohol [a mixture of cetyl alcohol ($C_{16}H_{33}OH$) and stearyl alcohol ($C_{18}H_{37}OH$)], lanolin alcohols (wool wax alcohols which are the unsaponifiable alcohol fraction of wool wax which is obtained following saponification of wool wax). Cetyl and cetylstearyl alcohol are particularly preferred.

It is advantageous according to the invention to choose the weight ratios of emulsifier A to emulsifier B to emulsifier C (A:B:C) as a:b:c, where a, b and c, independently of one another, may be rational numbers from 1 to 5, preferably from 1 to 3. A weight ratio of, for example, 1:1:1 is particularly preferred.

For the purposes of the present invention, it is advantageous to choose the total amount of the emulsifiers A and B and of coemulsifier C from the range from 2 to 20% by weight, advantageously from 5 to 15% by weight, in particular from 7 to 13% by weight, in each case based on the total weight of the formulation.

Pickering/Solids-Stabilized Emulsions

Also particularly advantageous for the purposes of the present invention are cosmetic or dermatological preparations which have been stabilized only by very finely divided solids particles. Such "emulsifier-free" emulsions are also referred to as Pickering emulsions.

In Pickering emulsions, the solid material accumulates at the oil/water interface in the form of a layer, as a result of which coalescence of the disperse phases is prevented. Of essential importance here are, in particular, the surface properties of the solids particles, which should exhibit both hydrophilic and also lipophilic properties.

The stabilizing solids particles can also advantageously be treated ("coated") to repel water, the intention being to form or retain an amphiphilic character of these solids particles. The surface treatment can consist in providing the solids particles with a thin hydrophobic or hydrophilic coat by processes known per se.

The average particle diameter of the microfine solids particles used as stabilizer is preferably chosen to be less than 100 µm, particularly advantageously less than 50 µm. In this connection, it is essentially unimportant in what form (platelets, rods, spheres, etc.) or modifications the solids particles used are present.

The microfine solids particles are preferably chosen from the group of amphiphilic metal oxide pigments. In particular,
  titanium dioxides (coated and uncoated): e.g. Eusolex T-2000 from Merck, titanium dioxide MT-100 Z from Tayca Corporation
  zinc oxides, e.g. Z-Cote and Z-Cote HP1 from BASF AG, MZ-300, MZ-500 and MZ-505M from Tayca Corporation
  iron oxides are advantageous.

Furthermore, it is advantageous when the microfine solids particles are chosen from the following group: boron nitrides, starch derivatives (tapioca starch, sodium corn starch octynyl succinate etc.), talc, latex particles.

It is advantageous according to the invention when the solids-stabilized emulsions comprise significantly less than 0.5% by weight of one or more emulsifiers or are even entirely emulsifier-free.

Sticks

Also advantageous for the purposes of the invention are preparations in the form of sticks. Viewed technically, most stick formulations are anhydrous fatty mixtures of solid or semisolid waxes and liquid oils, where highly purified paraffin oils and paraffin waxes are the stick base.

Customary bases for stick preparations are, for example, liquid oils (such as, for example, paraffin oils, castor oil, isopropyl myristate, $C_{12-15}$ alkyl benzoate), semisolid constituents (e.g. vaseline, lanolin), solid constituents (e.g. beeswax, ceresin and microcrystalline waxes and ozokerite)

or high-melting waxes (e.g. carnauba wax, candelilla wax). Water-containing stick preparations are also known per se, it being possible for these also to be present in the form of W/O emulsions.

The cosmetic or dermatological light-protective formulations according to the invention can have the customary composition and be used for cosmetic or dermatological light-protective, and also for the treatment, care and cleansing of the skin or of the hair and as a make-up product in decorative cosmetics.

Depending on their formulation, cosmetic or topical dermatological compositions for the purposes of the present invention can, for example, be used as skin protection cream, cleansing milk, day or night cream etc. It is optionally possible and advantageous to use the compositions according to the invention as a base for pharmaceutical formulations.

For use, the cosmetic and dermatological preparations are applied to the skin or the hair in an adequate amount in the manner customary for cosmetics.

The cosmetic and dermatological preparations according to the invention can comprise cosmetic auxiliaries as are customarily used in such preparations, e.g. preservatives, preservative aids, complexing agents, bactericides, perfumes, substances for preventing or increasing foaming, dyes, pigments which have a coloring action, thickeners, moisturizing or humectant substances, fillers which improve the feel on the skin, fats, oils, waxes or other customary constituents of a cosmetic or dermatological formulation, such as alcohols, polyols, polymers, foam stabilizers, electrolytes, organic solvents or silicone derivatives.

Advantageous preservatives for the purposes of the present invention are, for example, formaldehyde donors (such as, for example, DMDM hydantoin, which is available, for example, under the trade name Glydant™ from Lonza), iodopropyl butylcarbamates (e.g. those available under the trade names Glycacil-L, Glycacil-S from Lonza, or Dekaben LMB from Jan Dekker), parabens (i.e. alkyl p-hydroxybenzoates, such as methyl-, ethyl-, propyl- or butylparaben), phenoxyethanol, ethanol, benzoic acid and the like. In addition, the preservative system according to the invention also usually advantageously comprises preservative aids, such as, for example, octoxyglycerol, glycine soya etc.

Advantageous complexing agents for the purposes of the present invention are, for example, EDTA, [S,S]-ethylenediamine disuccinate (EDDS), which is available, for example, under the trade name Octaquest from Octel, pentasodium ethylenediamine tetramethylenephosphonate, which is available, for example, under the trade name Dequest 2046 from Monsanto and iminodisuccinic acid, which is available, inter alia, from Bayer AG under the trade names Iminodisuccinate VP OC 370 (about 30% strength solution) and Baypure CX 100 solid.

Particularly advantageous preparations are also obtained when antioxidants are used as additives or active ingredients. According to the invention, the preparations advantageously comprise one or more antioxidants. Favorable, but nevertheless optional, antioxidants which may be used are all antioxidants customary or suitable for cosmetic or dermatological applications.

For the purposes of the present invention, water-soluble antioxidants may be used particularly advantageously, such as, for example, vitamins, e.g. ascorbic acid and derivatives thereof.

Preferred antioxidants are also vitamin E and derivatives thereof, and vitamin A and derivatives thereof.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E or derivatives thereof are the antioxidant or the antioxidants, it is advantageous to choose their respective concentrations from the range from 0.001 to 10% by weight, based on the total weight of the formulation.

If vitamin A or vitamin A derivatives, or carotenes or derivatives thereof are the antioxidant or the antioxidants, it is advantageous to choose their respective concentrations from the range from 0.001 to 10% by weight, based on the total weight of the formulation.

It is particularly advantageous when the cosmetic preparations according to the present invention comprise cosmetic or dermatological active ingredients, preferred active ingredients being antioxidants which can protect the skin against oxidative stress.

Further advantageous active ingredients for the purposes of the present invention are natural active ingredients or derivatives thereof, such as, for example, α-lipoic acid, phytoene, D-biotin, coenzyme Q10, α-glucosylrutin, carnitine, carnosine, natural or synthetic isoflavonoids, creatine, taurine or β-alanine, and 8-hexadecene-1,16-dicarboxylic acid (dioic acid, CAS number 20701-68-2; provisional INCI name Octadecenedioic acid).

Formulations according to the invention which comprise, for example, known antiwrinkle active ingredients, such as flavone glycosides (in particular α-glycosylrutin), coenzyme Q10, vitamin E and derivatives and the like are particularly advantageously suitable for the prophylaxis and treatment of cosmetic or dermatological changes in the skin, as arise, for example, during the skin aging (such as, for example, dryness, roughness and formation of dryness wrinkles, itching, reduced refatting (e.g. after washing), visible vascular dilations (telangiectases, cuperosis), flaccidity and formation of wrinkles and lines, local hyperpigmentation, hypopigmentation and incorrect pigmentation (e.g. age spots), increased susceptibility to mechanical stress (e.g. cracking) and the like). In addition, they are advantageously suitable to counter the appearance of dry or rough skin.

The water phase of the preparations according to the invention can advantageously comprise customary cosmetic auxiliaries, such as, for example, alcohols, in particular those of low carbon number, preferably ethanol or isopropanol, diols or polyols of low carbon number, and ethers thereof, preferably propylene glycol, glycerol, butylene glycol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, and in particular one or more thickeners, which may advantageously be chosen from the group consisting of silicon dioxide, aluminum silicates or polysaccharides or derivatives thereof, e.g. hyaluronic acid, xanthan gum, hydroxypropylmethylcellulose, particularly advantageously from the group of polyacrylates, preferably a polyacrylate from the group of so-called Carbopols [from Bf. Goodrich], for example Carbopol grades 980, 981, 1382, 2984, 5984, ETD 2020, ETD 2050, Ultrez 10, in each case individually or in combination.

In addition, the preparations according to the invention can advantageously also comprise self-tanning substances, such as, for example, dihydroxyacetone or melanin derivatives in concentrations of from 1% by weight to 8% by weight, based on the total weight of the preparation.

In addition, the preparations according to the invention can advantageously also comprise repellents for protection against flies, ticks and spiders and the like. For example, N,N-diethyl-3-methylbenzamide (trade name: Meta-delphene, "DEET"), dimethyl phthalate (trade name: Palatinol M, DMP) and in particular ethyl 3-(N-n-butyl-N-acetylamino)propionate (available under the trade name Insekt Repellent® 3535 from Merck). The repellents can either be used individually or in combination.

Moisturizers is the term used to refer to substances or mixtures of substances which impart to cosmetic or dermatological preparations the property, following application or distribution on the surface of the skin, of reducing moisture release by the horny layer (also called trans-epidermal water loss (TEWL)) or of positively influencing hydration of the horny layer.

Advantageous moisturizers for the purposes of the present invention are, for example, glycerol, lactic acid, and lactates, in particular sodium lactate, butylene glycol, propylene glycol, biosaccharide gum-1, glycine soya, ethylhexyloxyglycerol, pyrrolidone-carboxylic acid and urea. In addition, it is particularly advantageous to use polymeric moisturizers from the group of water-soluble or water-swellable or water-gelable polysaccharides. Hyaluronic acid, chitosan, and a fucose-rich polysaccharide, which is filed in the Chemical Abstracts under the registry number 178463-23-5 and which is available, for example, under the name Fucogel® 1000 by SOLABIA S.A., for example, are particularly advantageous. Moisturizers can advantageously also be used as anti-wrinkle active ingredients for the prophylaxis and treatment of cosmetic or dermatological changes in the skin, as arise, for example, during skin aging.

The cosmetic or dermatological preparations according to the invention can also advantageously, but not necessarily, comprise fillers, which, for example, further improve the sensory and cosmetic properties of the formulations and, for example, bring about or enhance a velvety or silky feel on the skin. Advantageous fillers for the purposes of the present invention are starch and starch derivatives (such as, for example, tapioca starch, distarch phosphate, aluminum or sodium starch octenylsuccinate and the like), pigments which have neither a primarily UV filter effect nor a coloring effect (such as, for example, boron nitride etc.), and Aerosils® (CAS No. 7631-86-9).

The oil phase of the formulations according to the invention is advantageously chosen from the group of polar oils, for example from the group of lecithins and of fatty acid triglycerides, namely the triglycerol esters of saturated or unsaturated, branched or unbranched alkanecarboxylic acids with a chain length of from 8 to 24, in particular 12 to 18, carbon atoms. The fatty acid triglycerides can, for example, advantageously be chosen from the group of synthetic, semisynthetic and natural oils, such as, for example, cocoglyceride, olive oil, sunflower oil, soybean oil, peanut oil, rapeseed oil, almond oil, palm oil, coconut oil, castor oil, wheatgerm oil, grapeseed oil, thistle oil, evening primrose oil, macadamia nut oil and the like.

Also advantageous according to the invention are, for example, natural waxes of animal and vegetable origin, such as, for example, beeswax and other insect waxes, and berry wax, shea butter and lanolin (wool wax).

For the purposes of the present invention, further advantageous polar oil components can also be chosen from the group of esters of saturated or unsaturated, branched or unbranched alkanecarboxylic acids with a chain length of from 3 to 30 carbon atoms and saturated or unsaturated, branched or unbranched alcohols with a chain length of from 3 to 30 carbon atoms, and from the group of esters of aromatic carboxylic acids and saturated or unsaturated, branched or unbranched alcohols with a chain length of from 3 to 30 carbon atoms. Such ester oils can then advantageously be chosen from the group consisting of octyl palmitate, octyl cocoate, octyl isostearate, octyldodeceyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as, for example, jojoba oil.

In addition, the oil phase can advantageously be chosen from the group of dialkyl ethers and dialkyl carbonates, advantageous examples being dicaprylyl ether (Cetiol OE) and dicaprylyl carbonate, for example, that are available under the trade name Cetiol CC from Cognis.

It is also preferred the oil component or components from the group consisting of isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethyl isosorbide. It is particular advantageous if the oil phase of the formulations according to the invention has a content of $C_{12-15}$-alkyl benzoate or consists entirely of this.

Advantageous oil components are also, for example, butyloctyl salicylate (for example that available under the trade name Hallbrite BHB from CP Hall), hexadecyl benzoate and butyloctyl benzoate and mixtures thereof (Hallstar AB) and diethylhexyl naphthalate (Hallbrite TQ or Corapan TQ from H&R).

Any mixtures of such oil and wax components can also be used advantageously for the purposes of the present invention.

In addition, the oil phase can likewise advantageously also comprise nonpolar oils, for example those which are chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Among the polyolefins, polydecenes are the preferred substances.

The oil phase can also advantageously have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are joined via oxygen atoms in a chain-like or reticular manner, and the remaining valences of the silicon are saturated by hydrocarbon radicals (in most cases methyl groups, more rarely ethyl, propyl, phenyl groups etc.). Systematically, the silicone oils are referred to as polyorganosiloxanes. The methyl-substituted polyorganosiloxanes, which represent the most significant compounds of this group in terms of amount and are characterized by the following structural formula

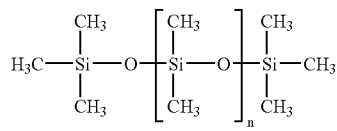

are also referred to polydimethylsiloxane or Dimethicone (INCI). Dimethicones have various chain lengths and have various molecular weights.

Particularly advantageous polyorganosiloxanes for the purposes of the present invention are, for example, dimethylpolysiloxanes [(poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (Octamethylcyclotetrasiloxane and decamethylcyclopentasiloxane), which are also referred to in accordance with INCI as Cyclomethicone, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Th. Goldschmidt. However, other silicone oils are also to be used advantageously for the purposes of the present invention, for example cetyldimethicone, hexamethylcyclotrisiloxane, polydimethylsiloxane, poly(methylphenylsiloxane).

The preparations according to the invention can also advantageously comprise one or more substances from the following group of siloxane elastomers, for example in order to increase the water resistance or the light-protective factor of the products:

(a) siloxane elastomers which contain the units $R_2SiO$ and $RSiO_{1.5}$ or $R_3SiO_{0.5}$ or $SiO_2$,
where the individual radicals R, in each case independently of one another, are hydrogen, $C_{1-24}$-alkyl (such as, for example, methyl, ethyl, propyl) or aryl (such as, for example, phenyl or tolyl), alkenyl (such as, for example, vinyl), and the weight ratio of the units $R_2SiO$ to $RSiO_{1.5}$ is chosen from the range from 1:1 to 30:1;

(b) siloxane elastomers which are insoluble and swellable in silicone oil and which are obtainable by the addition reaction of an organopolysiloxane (1) which contains silicon-bonded hydrogen with an organopolysiloxane (2) which contains unsaturated aliphatic groups,
where the quantitative amounts used are chosen such that the amount of hydrogen in the organopolysiloxane (1) or in the unsaturated aliphatic groups of the organopolysiloxane (2)
is in the range from 1 to 20 mol % when the organopolysiloxane is noncyclic and
is in the range from 1 to 50 mol % when the organopolysiloxane is cyclic.

For the purposes of the present invention, the siloxane elastomer or elastomers are advantageously present in the form of spherical powders or in the form of gels.

Siloxane elastomers present in the form of spherical powders which are advantageous according to the invention are those with the INCI name DimethiconeNinyl Dimethicone Crosspolymer, for example that available from DOW CORNING under the trade names DOW CORNING 9506 Powder.

It is particularly preferred when the siloxane elastomer is used in combination with oils from hydrocarbons of animal or vegetable origin, synthetic oils, synthetic esters, synthetic ethers or mixtures thereof.

It is very particularly preferred when the siloxane elastomer is used in combination with unbranched silicone oils which are liquid or pasty at room temperature or cyclic silicone oils or mixtures thereof. Organopolysiloxane elastomers with the INCI name Dimethicone/Polysilicone-11, very particularly the Gransil grades obtainable from Grant Industries Inc. GCM, GCM-5, DMG-6, CSE gel, PM-gel, LTX, ININ gel, AM-18 gel and DMCM-5 are particularly advantageous.

It is very extremely preferred when the siloxane elastomer is used in the form of a gel of siloxane elastomer and a lipid phase where the content of the siloxane elastomer in the gel is 1 to 80% by weight, preferably 0.1 to 60% by weight, in each case based on the total weight of the gel.

It is advantageous for the purposes of the present invention to choose the total amount of the siloxane elastomers (active content) from the range from 0.01 to 10% by weight, advantageously from 0.1 to 5% by weight, in each case based on the total weight of the formulation.

The cosmetic and dermatological preparations according to the invention can comprise dyes or color pigments, particularly when they are in the form of decorative cosmetics. The dyes and color pigments can be chosen from the corresponding positive list in the Cosmetics Directive or the EC list of cosmetic colorants. In most cases, they are identical to dyes approved for foods. Advantageous color pigments are, for example, titanium dioxide, mica, iron oxides (e.g. $Fe_2O_3$, $Fe_3O_4$, $FeO(OH)$) and tin oxide. Advantageous dyes are, for example, carmine, Prussian blue, chromium oxide green, ultramarine blue and manganese violet. It is particularly advantageous to choose the dyes or the color pigments from the *Rowe Colour Index, 3$^{rd}$ Edition, Society of Dyers and Colourists, Bradford, England,* 1971.

If the formulations according to the invention are in the form of products which are used on the face, it is favorable to choose one or more substances from the following group as the dye: 2,4-dihydroxyazobenzene, 1-(2'-chloro-4'-nitro-1'-phenylazo)-2-hydroxynaphthalene, Ceres red, 2-(sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthyl-6-sulfonic acid, aluminum salt of 1-(4-sulfo-1-naphthylazo)-2-naphthyl-3,6-disulfonic acid, 1-(4-sulfo-1-naphthylazo)-2-naphthol-6,8-disulfonic acid, aluminum salt of 4-(4-sulfo-1-phenylazo)-1-(4-sulfophenyl)-5-hydroxypyrazolone-3-carboxylic acid, aluminum and zirconium salts of 4,5-dibromofluorescein, aluminum and zirconium salts of 2,4,5,7-tetrabromofluorescein, 3',4',5',6'-tetrachloro-2,4,5,7-tetrabromofluorescein and its aluminum salt, aluminum salt of 2,4,5,7-tetraiodofluorescein, aluminum salt of quinophthalonedisulfonic acid, aluminum salt of indigodisulfonic acid, red and black iron oxide (CIN: 77 491 (red) and 77 499 (black)), iron oxide hydrate (CIN: 77 492), manganese ammonium diphosphate and titanium dioxide.

Also advantageous are oil-soluble natural dyes, such as, for example, paprika extracts, β-carotene or cochineal.

Also advantageous for the purposes of the present invention are formulations with a content of pearlescent pigments. Preference is given in particular to the types of pearlescent pigments listed below:

1. Natural pearlescent pigments, such as, for example,
    "pearlessence" (guanine/hypoxanthin mixed crystals from fish scales) and
    "mother-of-pearl" (ground mussel shells)
2. Monocrystalline pearlescent pigments, such as, for example, bismuth oxychloride (BiOCl)
3. Layer-substrate pigments: e.g. mica/metal oxide Bases for pearlescent pigments are, for example, pulverulent pigments or castor oil dispersions of bismuth oxychloride or titanium dioxide, and bismuth oxychloride or titanium dioxide on mica. The luster pigment listed under CIN 77163, for example, is particularly advantageous.

Also advantageous are, for example, the following types of pearlescent pigments based on mica/metal oxide:

| Group | Coating/layer thickness | Color |
| --- | --- | --- |
| Silver-white pearlescent pigments | $TiO_2$: 40-60 nm | Silver |
| Interference pigments | $TiO_2$: 60-80 nm | Yellow |
|  | $TiO_2$: 80-100 nm | Red |
|  | $TiO_2$: 100-140 nm | Blue |
|  | $TiO_2$: 120-160 nm | Green |
| Color luster pigments | $Fe_2O_3$ | Bronze |
|  | $Fe_2O_3$ | Copper |
|  | $Fe_2O_3$ | Red |
|  | $Fe_2O_3$ | Red-violet |
|  | $Fe_2O_3$ | Red-green |
|  | $Fe_2O_3$ | Black |
| Combination pigments | $TiO_2/Fe_2O_3$ | Gold shades |
|  | $TiO_2/Cr_2O_3$ | Green |
|  | $TiO_2$/Prussian blue | Deep blue |
|  | $TiO_2$/carmine | Red |

Particular preference is given, for example, to the pearlescent pigments obtainable from Merck under the trade names Timiron, Colorona or Dichrona.

The list of given pearlescent pigments is not of course intended to be limiting. Pearlescent pigments which are advantageous for the purposes of the present invention are obtainable by numerous methods known per se. For example, other substrates apart from mica can be coated with further metal oxides, such as, for example, silica and the like. $SiO_2$ particles coated with, for example, $TiO_2$ and $Fe_2O_3$ ("ronaspheres"), which are sold by Merck and are particularly suitable for the optical reduction of fine lines, are suitable.

It can, moreover, be advantageous to dispense completely with a substrate such as mica. Particular preference is given to iron pearlescent pigments prepared without the use of mica. Such pigments are obtainable, for example, under the trade name Sicopearl Kupfer 1000 from BASF.

In addition, also particularly advantageous are effect pigments which are obtainable under the trade name Metasomes Standard/Glitter in various colors (yellow, red, green, blue) from Flora Tech. The glitter particles are present here in mixtures with various auxiliaries and dyes (such as, for example, the dyes with the Colour Index (CI) numbers 19140, 77007, 77289, 77491).

The dyes and pigments may be present either individually or in a mixture, and can be mutually coated with one another, different coating thicknesses generally giving rise to different color effects. The total amount of dyes and color-imparting pigments is advantageously chosen from the range from, for example, 0.1% by weight to 30% by weight, preferably from 0.5 to 15% by weight, in particular from 1.0 to 10% by weight, in each case based on the total weight of the preparations.

For the purposes of the present invention, it is also advantageous to provide cosmetic and dermatological preparations whose main purpose is not protection against sunlight, but which nevertheless have a content of further UV protection substances. Thus, for example, UV-A and/or UV-B filter substances are usually incorporated into daycreams or make-up products. UV protection substances, like antioxidants and, if desired, preservatives, also constitute effective protection of the preparations themselves against spoilage. Also favorable are cosmetic and dermatological preparations in the form of a sunscreen.

Accordingly, for the purposes of the present invention, the preparations preferably additionally comprise at least one further UV-A, UV-B, or broadband filter substance. The formulations can, but do not necessarily, optionally comprise one or more organic or inorganic pigments as UV filter substances, which may be present in the water phase and/or the oil phase.

In addition, the preparations according to the invention can also advantageously be in the form of so-called oil-free cosmetic or dermatological emulsions, which comprise a water phase and at least one UV filter substance which is liquid at room temperature as a further phase.

For the purposes of the present invention, particularly advantageous UV filter substances which are liquid at room temperature are homomenthyl salicylate (INCI: Homosalate), 2-ethylhexyl 2-cyano-3,3-diphenylacrylate (INCI: Octocrylene), 2-ethylhexyl 2-hydroxybenzoate (2-ethylhexyl salicylate, octyl salicylate, INCI: Octyl Salicylate) and esters of cinnamic acid, preferably 2-ethylhexyl 4-methoxycinnamate (INCI: Octyl Methoxycinnamate) and isopentyl 4-methoxycinnamate (INCI: Isoamyl p-Methoxycinnamate), 3-(4-(2,2-bisethoxycarbonylvinyl)phenoxy)propenyl)methoxy-siloxane/dimethylsiloxane copolymer, which is available, for example, under the trade name Parsol® SLX from Hoffmann La Roche.

Preferred inorganic pigments are metal oxides or other metal compounds which are insoluble or sparingly soluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and also the sulfate of barium ($BaSO_4$).

For the purposes of the present invention, the pigments may advantageously also be used in the form of commercially available oily or aqueous predispersions. Dispersion auxiliaries or solubility promoters may advantageously be added to these predispersions.

According to the invention, the pigments may advantageously be surface-treated ("coated"), the intention being to form or retain, for example, a hydrophilic, amphiphilic or hydrophobic character. This surface treatment can consist in providing the pigments with a thin hydrophilic or hydrophobic inorganic or organic coat by methods known per se. For the purposes of the present invention, the various surface coatings may also comprise water.

Inorganic surface coatings for the purposes of the present invention may consist of aluminum oxide ($Al_2O_3$), aluminum hydroxide $Al(OH)_3$, or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may be present on their own, in combination or in combination with organic coating materials.

Organic surface coatings for the purposes of the present invention may consist of vegetable or animal aluminum stearate, vegetable or animal stearic acid, lauric acid, dimethylpolysiloxane (also: Dimethicone), methylpolysiloxane (Methicone), simethicone (a mixture of dimethylpolysiloxane with an average chain length of from 200 to 350 dimethylsiloxane units and silica gel) or alginic acid. These organic surface coatings may be present on their own, in combination or in combination with inorganic coating materials.

Zinc oxide particles and predispersions of zinc oxide particles which are suitable according to the invention are obtainable under the following trade names from the companies listed:

| Trade name | Coating | Manufacturer |
|---|---|---|
| Z-Cote HP1 | 2% Dimethicone | BASF |
| Z-Cote | / | BASF |
| ZnO NDM | 5% Dimethicone | H&R |
| MZ-303S | 3% Methicone | Tayca Corporation |
| MZ-505S | 5% Methicone | Tayca Corporation |

Suitable titanium dioxide particles and predispersions of titanium dioxide particles are available under the following trade names from the companies listed:

| Trade name | Coating | Manufacturer |
|---|---|---|
| MT-100TV | Aluminum hydroxide/stearic acid | Tayca Corporation |
| MT-100Z | Aluminum hydroxide/stearic acid | Tayca Corporation |
| Eusolex T-2000 | Alumina/Simethicone | Merck KgaA |
| Titanium dioxide T805 (Uvinul TiO$_2$) | Octyltrimethylsilane | Degussa |
| Tioveil AQ 10PG | Alumina/Silica | Solaveil/Uniquema |
| Eusolex T-aqua | Water/alumina/sodium metaphosphate | Merck |

Further advantageous pigments are latex particles. Latex particles advantageous according to the invention are those described in the following specifications: U.S. Pat. No. 5,663,213 and EP 0 761 201. Particularly advantageous latex particles are those which are formed from water and styrene/acrylate copolymers and are available, for example, under the trade name "Alliance SunSphere" from Rohm & Haas.

Advantageous UV-A filter substances for the purposes of the present invention are dibenzoylmethane derivatives, in particular 4-(tert-butyl)-4'-methoxydibenzoyl-methane (CAS No. 70356-09-1), which is sold by Givaudan under the name Parsol® 1789 and by Merck under the trade name Eusolex® 9020.

Advantageous further UV filter substances for the purposes of the present invention are sulfonated, water-soluble UV filters, such as, for example:

Phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic acid bis-sodium salt with the INCI name Disodium Phenyl Dibenzimidazole Tetrasulfonate (CAS No.: 180898-37-7), which is available, for example, under the trade name Neo Heliopan AP from Haarmann & Reimer;

Salts of 2-phenylbenzimidazole-5-sulfonic acid, such as its sodium, potassium or its triethanolammonium salt, and the sulfonic acid itself with the INCI name Phenylbenzimidazole Sulfonic Acid (CAS No. 27503-81-7), which is available under the trade name Eusolex 232 from Merck, or under Neo Heliopan Hydro from Haarmann & Reimer;

1,4-di(2-oxo-10-sulfo-3-bornylidenemethyl)benzene (also: 3,3'-(1,4-phenylene-dimethylene)bis(7,7-dimethyl-2-oxobicyclo[2.2.1]hept-1-ylmethanesulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di (2-oxo-3-bornylidenemethyl-10-sulfonic acid) has the INCI name Terephthalidene Dicamphor Sulfonic Acid (CAS No.: 90457-82-2) and is available, for example, under the trade name Mexoryl SX from Chimex;

sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and salts thereof.

Advantageous UV filter substances for the purposes of the present invention are also so-called broadband filters, i.e. filter substances which absorb both UV-A and also UV-B radiation.

Advantageous broadband filters or UV-B filter substances are, for example, triazine derivatives, such as, for example, 2,4-bis{[4-(2-ethylhexyloxy)-2-hydroxy]phenyl}-6-(4-methoxyphenyl)-1,3,5-triazine (INCI: BisEthylhexyloxyphenol Methoxyphenyl Triazine), which is available under the trade name Tinosorb® S from CIBA-Chemikalien GmbH;

dioctylbutylamidotriazone (INCI: Dioctylbutamidotriazone), which is available under the trade name UVA-SORB HEB from Sigma 3V;

Tris(2-ethylhexyl) 4,4',4"-(1,3,5-triazine-2,4,6-triyltriimino)trisbenzoate, also: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150;

2-[4,6-bis(2,4-dimethylphenyl)-1,3,5-triazin-2-yl]-5-(octyloxy)phenol (CAS No.: 2725-22-6).

An advantageous broadband filter for the purposes of the present invention is also 2,2'-methylenebis(6-(2H-benzotriazol-2-yl)-4-(1,1,3,3-tetramethylbutyl)phenol), which is available under the trade name Tinosorb® M from CIBA-Chemikalien GmbH.

For the purposes of the present invention, an advantageous broadband filter is a 1 so 2-(2H-benzotriazol-2-yl)-4-methyl-6-[2-methyl-3-[1,3,3,3-tetramethyl-1-[(trimethyl-silyl)oxy]disiloxanyl]propyl]phenol (CAS No.: 155633-54-8) with the INCI name Drometrizole Trisiloxane.

The further UV filter substances may be oil-soluble or water-soluble. Advantageous oil-soluble filter substances are, for example:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethyl-amino)benzoate, amyl 4-(dimethylamino) benzoate;

2,4,6-trianilino(p-carbo-2'-ethyl-1'-hexyloxy)-1,3,5-triazine;

esters of benzalmalonic acid, preferably di(2-ethylhexyl) 4-methoxybenzalmalonate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxy-benzophenone and UV filters bonded to polymers.

Advantageous water-soluble filter substances are, for example: Sulfonic acid derivatives of 3-benzylidenecamphor, such as, for example, 4-(2-oxo-3-bornylidenemethyl) benzenesulfonic acid, 2-methyl-5-(2-oxo-3-bornylidenemethyl)sulfonic acid and salts thereof.

A further light-protective filter substance to be used advantageously according to the invention is ethylhexyl 2-cyano-3,3-diphenylacrylate (octocrylene), which is available from BASF under the name Uvinul® N 539 T.

However it is of particular advantage according to the invention if the preparations of the invention are free of ethylhexyl 2-cyano-3,3-diphenylacrylate (octocrylene).

Besides the filter substance(s) according to the invention, particularly advantageous preparations for the purposes of the present invention which are characterized by high or very high UV-A protection preferably also comprise further UV-A or broadband filters, in particular dibenzoylmethane derivatives [for example 4-(tert-butyl)-4'-methoxydibenzoylmethane] or 2,4-bis{[4-(2-ethylhexyloxy)-2-hydroxy]phenyl}-6-(4-methoxyphenyl)-1,3,5-triazine or phenylene-1,4-bis(2-benzimidazyl)-3,3'-5,5'-tetrasulfonic acid bis-sodium salt, in each case individually or in any combinations with one another.

The list of given UV filters which can be used for the purposes of the present invention is not of course intended to be limiting.

The preparations according to the invention advantageously comprise the substances which absorb UV radiation in the UV-A and/or UV-B region in a total amount of, for example, from 0.1% by weight to 30% by weight, preferably from 0.5 to 20% by weight, in particular 1.0 to 15.0% by weight, in each case based on the total weight of the preparations, in order to provide cosmetic preparations which protect the hair or the skin from the entire range of ultraviolet radiation.

In addition, it may in some instances be advantageous to incorporate film formers into the cosmetic or dermatological preparations according to the invention, for example in order to improve the water resistance of the preparations, or to increase the UV protection performance (UV-A and/or UV-B boosting). Both water-soluble or dispersible and also fat-soluble film formers are suitable, in each case individually or in combination with one another.

Advantageous water-soluble or dispersible film formers are, for example, polyurethanes (e.g. the Avalure® grades from Goodrich), Dimethicone Copolyol Polyacrylate (Silsoft Surface® from the Witco Organa Silicones Group), PVPNA (VA=vinyl acetate) copolymer (Luviscol VA 64 Powder from BASF), $C_{20-40}$ carboxylic acid with polyethylene (Performacid 350 from New Phase Technologies) etc.

Advantageous fat-soluble film formers are, for example, the film formers from the group of polymers based on polyvinylpyrrolidone (PVP)

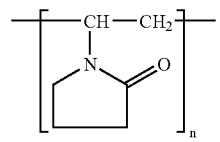

Particular preference is given to copolymers of polyvinylpyrrolidone, for example the PVP hexadecene copolymer and the PVP eicosene copolymer, which are available under the trade names Antaron V216 and Antaron V220 from GAF Chemicals Cooperation, and also Tricontayl PVP and the like.

The examples below are intended to illustrate the present invention without limiting it. The numerical values in the examples are percentages by weight, based on the total weight of the respective preparations.

EXAMPLES

In the following examples:

| 1. O/W sunscreen emulsions | | | | | | | |
|---|---|---|---|---|---|---|---|
| | 1 | 2 | 3 | 4 | 5 | 6 | 7 |
| Glycerol monostearate SE | 0.50 | 1.00 | 3.00 | | | 1.50 | |
| Glyceryl stearate citrate | 2.00 | | | 1.00 | 2.00 | | 2.50 |
| Stearic acid | | 3.00 | 0.75 | 2.00 | | | |
| PEG-40 stearate | 0.50 | | | | | 2.00 | |
| PEG-100 stearate | | | 1.50 | | | | |
| Lauryl methicone copolyol | | | | 0.75 | | 0.50 | |
| Cetyl phosphate | | | 0.75 | | 1.00 | | |
| Stearyl alcohol | | | 3.00 | | | 2.00 | 0.50 |
| Cetyl alcohol | 2.50 | 1.00 | | | 0.50 | | 2.00 |
| UVASorb ® K2A | 1.00 | 2.50 | 3.00 | 4.00 | 1.50 | 5.00 | 1.00 |
| Uvinul ® A Plus | 3.00 | 2.50 | 0.50 | 0.25 | 1.00 | 0.50 | 4.00 |
| Bisethylhexyloxyphenol methoxyphenyltriazine | | 1.00 | | | | 1.00 | 0.50 |
| Disodium phenyl dibenzimidazole tetrasulfonate | | | | 1.00 | | 2.00 | |
| Ethylhexyltriazone | 2.00 | | | 2.00 | | 2.00 | |
| Diethylhexylbutamidotriazone | | 2.00 | | | | | |
| Ethylhexyl methoxycinnamate | | 3.50 | | 10.00 | | | |
| Octocrylene | | | | 5.00 | 9.00 | 7.50 | 2.50 |
| Methylenebisbenztriazolyl tetramethylbutylphenol | | 2.00 | | 3.00 | | | |

-continued

1. O/W sunscreen emulsions

| | 1 | 2 | 3 | 4 | 5 | 6 | 7 |
|---|---|---|---|---|---|---|---|
| Ethylhexyl salicylate | | | 3.00 | | | | 5.00 |
| Drometrizole trisiloxane | | | 0.50 | | | 1.00 | |
| Titanium dioxide T 805 | | 1.50 | | | 1.00 | 0.50 | |
| Titanium dioxide MT-100Z | 1.00 | | | 3.00 | 1.00 | | |
| C12-15 alkyl benzoate | | 2.50 | | | | 7.00 | 5.00 |
| Dicaprylyl ether | | | 3.50 | | 2.00 | | |
| Butylene glycol dicaprylate/dicaprate | 5.00 | | | 5.00 | 3.00 | | |
| Cetearyl isononanoate | | 4.00 | | | | 2.00 | 2.00 |
| Dimethicone | | 0.50 | 1.00 | | 2.00 | | |
| Cyclomethicone | 2.00 | | | 4.50 | | | 0.50 |
| Dimethicone/vinyl dimethicone crosspolymer | | 4.00 | | | | | 0.50 |
| PVP hexadecene copolymer | 0.50 | | | 0.50 | 1.00 | | 1.00 |
| Glycerol | 3.00 | 7.50 | | 7.50 | 5.00 | | 2.50 |
| Xanthan gum | 0.15 | | 0.05 | | | | 0.30 |
| Butylene glycol | | 5.00 | | | | 7.00 | |
| Vitamin E Acetate | 0.50 | | 0.25 | 0.50 | 0.75 | | 1.00 |
| Dioic acid | 0.25 | | | 0.20 | | 0.25 | |
| Fucogel ® 1000 | | | 1.50 | | | 5.00 | |
| DMDM hydantoin | | 0.60 | 0.40 | 0.20 | | | |
| Methylparaben | 0.15 | | 0.25 | | 0.50 | | |
| Phenoxyethanol | 1.00 | 0.40 | | 0.40 | 0.50 | | 0.60 |
| EDTA | | 0.20 | 0.35 | 0.50 | 0.02 | | 0.03 |
| Ethanol | | 2.00 | 1.50 | | 3.00 | 5.00 | 1.00 |
| Insect repellent 3535 | | | 5.00 | | | | |
| Perfume | 0.20 | 0.20 | | | | 0.30 | 0.40 |
| Water | ad 100 | ad 100 | ad 100 | ad 100 | ad 100 | ad 100 | ad 100 |

UVASorb ® K2A = 2,4-bis[5-1(dimethylpropyl)benzoxazol-2-yl-(4-phenyl)imino]-6-(2-ethylhexyl)imino-1,3,5-triazine [CAS No. 288254-16-0]
Uvinul ® A Plus = hexyl 2-(4'-diethylamino-2'-hydroxybenzoyl)benzoate (also: amino-benzophenone)

2. Foam-like O/W emulsions:

| | Emulsion 1 | | Emulsion 2 | |
|---|---|---|---|---|
| | % by wt. | % by vol. | % by wt. | % by vol. |
| Stearic acid | 5.00 | | 1.00 | |
| Cetyl alcohol | 5.50 | | | |
| Cetylstearyl alcohol | | | 2.00 | |
| PEG-40 stearate | 8.50 | | | |
| PEG-20 stearate | | | 1.00 | |
| Caprylic/capric triglycerides | 4.00 | | 2.00 | |
| C12-15 alkyl benzoate | 10.00 | | 15.50 | |
| Cyclomethicone | 4.00 | | | |
| Dimethicone | | | 0.50 | |
| Octyl isostearate | | | 5.00 | |
| Myristyl myristate | | | 2.00 | |
| Ceresine | 1.50 | | | |
| Glycerol | | | 3.00 | |
| UVASorb ® K2A | 2.00 | | 4.00 | |
| Uvinul A Plus ® | 2.00 | | 1.50 | |
| Terephthalidenecamphorsulfonic acid | 0.50 | | | |
| Drometrizole trisiloxane | 1.50 | | | |
| Ethylhexyl methoxycinnamate | 5.00 | | 4.00 | |
| Ethylhexyltriazone | | | 3.00 | |
| Octocrylene | 5.00 | | | |
| Titanium dioxide Uvinul T 805 | 1.00 | | | |
| BHT | | | 0.02 | |
| Na$_2$H$_2$EDTA | 0.50 | | 0.10 | |
| Perfume, preservative, | q.s. | | q.s. | |
| Dyes, etc. | q.s. | | q.s. | |
| Potassium hydroxide | q.s. | | q.s. | |
| Water | ad 100.00 | | ad 100.00 | |
| | pH adjusted to 6.5-7.5 | | pH adjusted to 5.0-6.0 | |
| Emulsion 1 | | 70 | | |
| Emulsion 2 | | | | 35 |
| Gas (nitrogen) | | 30 | | |
| Gas (helium) | | | | 65 |

Combining of the fatty/light-protective filter phase heated to 78° C. with the water/light-protective filter phase heated to 75° C. Homogenization using a toothed-wheel dispersing machine (rotor-stator principle) at 65° C. Stirring for 45 min in the Becomix with gassing with helium at 1 bar with cooling to 30° C. Addition of the additives at 30° C. (perfume). Homogenization by means of a toothed-wheel dispersing machine (rotor-stator principle) at 23° C.

3. PIT emulsions (for use as impregnation solution, spray or aerosol)

| | 1 | 2 | 3 | 4 | 5 | 6 | 7 | 8 |
|---|---|---|---|---|---|---|---|---|
| Glycerol monostearate SE | 0.50 | 2.00 | 3.00 | 5.00 | | | 0.50 | 4.00 |
| Glyceryl isostearate | | | | | 3.50 | 4.00 | 2.00 | |
| Isoceteth-20 | | 0.50 | | | 2.00 | | | |
| Ceteareth-12 | | 5.00 | | 1.00 | | | | 3.50 |
| Ceteareth-20 | | | | 2.00 | | 2.50 | 3.00 | |
| PEG-100 stearate | 5.00 | | 1.00 | | | | | 0.50 |
| Cetyl alcohol | 2.50 | 1.00 | | 1.50 | | 0.50 | 1.50 | |
| Cetyl palmitate | | | | 0.50 | | 1.00 | | |
| Lauryl methicone copolyol | | | 1.00 | | | | | 0.75 |
| Polyglyceryl-2 dipolyhydroxy-stearate | | | | 0.75 | 0.25 | | | |
| UVASorb ® K2A | 1.50 | 2.00 | 2.00 | 3.00 | 5.00 | 3.00 | 1.00 | 3.50 |
| Uvinul ® A Plus | 2.00 | 1.40 | 4.00 | 0.75 | 0.25 | 3.00 | 2.00 | 1.00 |
| Disodium phenyldi-benzimidazoletetrasulfonate | | 2.00 | | | | | | 2.00 |
| Terephthalidenedicamphor-sulfonic acid | | | | 0.50 | | | 1.00 | |
| Butylmethoxydibenzoyl-methane | | | 1.00 | | 2.00 | | 0.75 | |
| Drometrizole trisiloxane | | | 2.00 | | | 3.00 | | 1.00 |
| Ethylhexyl methoxycinnamate | 8.00 | | | 4.50 | 5.00 | 10.00 | | |
| Diethylhexylbutamidotriazone | | | | | 1.00 | | | 1.50 |
| Ethylhexyltriazone | 2.00 | | 2.00 | | | 2.00 | | 3.00 |
| Octocrylene | | | 5.00 | | 10.00 | | | 7.50 |
| C12-15 alkyl benzoate | 3.50 | | | | | | | |
| Cocoglycerides | | 3.00 | | 3.00 | | | | 3.50 |
| Dicaprylyl ether | 4.00 | | 2.00 | | | | | |
| Butylene glycol dicaprylate/dicaprate | | 4.00 | | | | | | |
| Dicaprylyl carbonate | | | 5.00 | | | | | 6.00 |
| Cyclomethicone | | | | | 2.00 | 6.00 | | |
| PVP hexadecene copolymer | | | | 1.00 | 1.50 | 0.50 | | |
| Glycerol | 10.0 | 5.00 | | 7.50 | | 10.00 | | |
| Vitamin E Acetate | 1.00 | | | 0.75 | 0.50 | | 1.00 | |
| 2,6-Diethylhexyl naphthalate | | | | 4.00 | 3.50 | | | 0.50 |
| Iodopropyl butylcarbamate | 0.12 | | | | 0.20 | | | |
| DMDM hydantoin | | | | 0.10 | | 0.05 | | |
| Methylparaben | | 0.50 | | | 0.45 | | | |
| Phenoxyethanol | 0.50 | 0.40 | | 1.00 | | | | 1.00 |
| Ethylhexyloxyglycerol | | 0.30 | | | 1.00 | 0.35 | | |
| Ethanol | | | 5.00 | | | | 7.50 | 4.00 |
| Dyes, water-soluble | | | | | 0.02 | 0.01 | | |
| Trisodium EDTA | | | 0.14 | | | 0.20 | | 0.50 |
| Perfume | 0.20 | | 0.20 | 0.20 | 0.45 | | | 0.20 |
| Water | ad 100 | ad 100 | ad 100 | ad 100 | ad 100 | ad 100 | ad 100 | ad 100 |

4. Low viscosity to sprayable W/O emulsions (for use as impregnation solution, spray or aerosol)

| | 1 | 2 | 3 | 4 | 5 |
|---|---|---|---|---|---|
| Cetyl dimethicone copolyol | 4.00 | | | 2.50 | 3.00 |
| Polyglyceryl-2 dipolyhydroxystearate | | | 3.00 | | 1.00 |
| Isostearyl diglyceryl succinate | | | 0.75 | | 0.30 |
| Lauryl methicone copolyol | | | | 2.00 | |
| Polysorbate-65 | | | 2.00 | | 1.50 |
| PEG-100 stearate | | | | 1.20 | 0.70 |
| Cetearyl sulfate | | | 0.25 | | 1.00 |
| Dimethicone | | 4.00 | | | 2.00 |
| Cyclomethicone | 12.00 | 20.00 | | 30.00 | 15.00 |
| UVASorb ® K2A | 2.00 | 1.50 | 3.00 | 0.50 | 5.00 |
| Uvinul ® A Plus | 3.50 | 2.00 | 0.50 | 4.00 | 0.25 |
| Bisethylhexyloxyphenol methoxyphenyltriazine | 1.00 | | | 0.50 | |
| Disodium phenyldibenzimidazoletetrasulfonate | | 1.50 | | | 2.00 |
| Drometrizole trisiloxane | | | | 1.00 | |
| Ethylhexyl methoxycinnamate | | 3.00 | 4.00 | | 10.00 |
| Ethylhexyl salicylate | | | | 5.00 | 3.50 |
| Octocrylene | | | 5.00 | 4.00 | |

4. Low viscosity to sprayable W/O emulsions (for use as impregnation solution, spray or aerosol)

| | 1 | 2 | 3 | 4 | 5 |
|---|---|---|---|---|---|
| Diethylhexylbutamidotriazone | | 1.00 | | | 6.50 |
| Ethylhexyltriazone | 3.00 | | | | 4.00 |
| Titanium dioxide MT-100 Z | | 0.50 | 1.00 | 1.50 | 0.50 |
| Zinc oxide Z-Cote | 2.00 | | | | 4.00 |
| Dicaprylyl carbonate | 5.00 | | 15.00 | | 4.00 |
| Dihexyl carbonate | | 10.00 | | | |
| C12-15 alkyl benzoate | 7.00 | | 10.00 | | |
| Mineral oil | 10.00 | | | | 6.00 |
| Cocoglycerides | | 2.00 | | 5.00 | |
| PVP hexadecene copolymer | | 0.75 | | | 0.40 |
| Glycerol | | | | 5.00 | 7.00 |
| α-Glucosylrutin | | | | | 0.15 |
| EDTA | | 0.15 | 0.03 | | 0.15 |
| Glycine soya | 0.75 | | | 1.50 | |
| Magnesium sulfate | 0.75 | 1.00 | | 0.45 | 1.00 |
| DMDM hydantoin | | 0.05 | | | 0.10 |
| Phenoxyethanol | 1.00 | 0.75 | 0.50 | | 1.00 |
| Ethanol | 2.00 | | | 5.00 | 1.00 |
| Dye, oil-soluble | 0.02 | | | | |
| Perfume | 0.30 | 0.45 | 0.35 | | 0.15 |
| Water | ad 100 | ad 100 | ad 100 | ad 100 | ad 100 |

5. W/O sunscreen emulsions (creams and lotions)

| | 1 | 2 | 3 | 4 | 5 |
|---|---|---|---|---|---|
| Cetyldimethicone copolyol | | | | 4.00 | |
| Polyglyceryl-2 dipolyhydroxystearate | 5.00 | 4.50 | | | 4.50 |
| PEG-30 dipolyhydroxystearate | | | 5.00 | 2.00 | |
| UVASorb ® K2A | 3.50 | 2.00 | 1.50 | 4.00 | 0.25 |
| Uvinul ® A Plus | 3.00 | 1.00 | 0.50 | 0.25 | 2.50 |
| Phenylbenzimidazolesulfonic acid | | 4.00 | | 2.00 | 0.50 |
| Ethylhexyl methoxycinnamate | | 8.00 | | 5.00 | 4.00 |
| Diethylhexylbutamidotriazone | 3.00 | 1.00 | | | 3.00 |
| Ethylhexyltriazone | | | 3.00 | 4.00 | |
| Octocrylene | 7.00 | | 8.00 | | 2.50 |
| Drometrizole trisiloxane | | | 3.00 | | |
| Titanium dioxide Uvinul ® T 805 | 2.00 | 1.00 | | | |
| Titanium dioxide MT-100 TV | | | 3.00 | | 2.00 |
| Zinc oxide Z-Cote ® HP1 | 2.50 | | 6.00 | | |
| Mineral oil | | | 10.0 | | 8.00 |
| Cocoglycerides | 4.00 | 6.50 | | | |
| C12-15 alkyl benzoates | | | | 9.00 | |
| Dicaprylyl ether | 10.00 | | | | 7.00 |
| Butylene glycol dicaprylate/dicaprate | | | 2.00 | 8.00 | 4.00 |
| Cyclomethicone | 2.00 | | | | 2.00 |
| PVP eicosene copolymer | 0.50 | | | 1.50 | 1.00 |
| Trisodium EDTA | 1.00 | | | 0.35 | |
| Ethylhexyloxyglycerol | | 0.30 | 1.00 | | 0.50 |
| Glycerol | 3.00 | 7.50 | | 7.50 | 2.50 |
| Butylene glycol | | | 10.00 | | 6.50 |
| Glycine soya | | 1.00 | 1.50 | | |
| MgSO4 | 1.00 | 0.50 | | 0.50 | |
| Vitamin E | 0.50 | | 0.25 | | 1.00 |
| DMDM hydantoin | | 0.60 | | 0.20 | |
| Methylparaben | 0.50 | | | 0.15 | |
| Phenoxyethanol | 0.50 | 0.40 | | 1.00 | 0.60 |
| Dihydroxyacetone | | | 5.50 | | |
| Ethanol | 3.00 | | 4.50 | | 1.00 |
| Perfume | 0.20 | | 0.20 | | 0.20 |
| Water | ad 100 | ad 100 | ad 100 | ad 100 | ad 100 |

6. Hydrodispersions (for use as lotion, impregnation solution or spray)

|  | 1 | 2 | 3 | 4 | 5 |
|---|---|---|---|---|---|
| PEG-40 stearate |  | 1.25 |  |  |  |
| Cetyl alcohol |  |  |  | 2.00 |  |
| Sodium carbomer |  | 0.20 |  | 0.30 |  |
| Acrylates/C10-30 alkyl acrylate crosspolymer |  |  | 0.40 | 0.10 | 0.10 |
| Xanthan gum | 0.50 | 0.30 | 0.15 |  | 0.50 |
| Dimethicone/vinyldimethicone crosspolymer |  |  | 5.00 |  | 3.00 |
| UVASorb ® K2A | 2.00 | 1.50 | 4.00 | 3.50 | 0.50 |
| Uvinul A ® Plus | 0.25 | 3.50 | 0.50 | 2.00 | 1.50 |
| Bisethylhexyloxyphenol methoxyphenyltriazine |  |  | 0.25 |  |  |
| Terephthalidenedicamphorsulfonic acid |  | 0.20 |  |  | 0.50 |
| Disodium phenyldibenzimidazoletetrasulfonate | 0.75 |  |  |  | 1.00 |
| Ethylhexyl methoxycinnamate |  |  |  | 5.00 | 8.00 |
| Methylenebisbenzotriazolyltetra-methylbutylphenol |  | 1.00 |  |  |  |
| Diethylhexylbutamidotriazone |  |  | 2.00 |  |  |
| Ethylhexyltriazone | 4.00 |  |  | 4.00 |  |
| Octocrylene |  | 4.00 | 10.00 |  | 2.50 |
| Titanium dioxide MT-100Z | 0.50 |  | 2.00 | 3.00 | 1.00 |
| C12-15 alkyl benzoates | 2.00 | 2.50 |  |  |  |
| Butylene glycol dicaprylate/dicaprate | 4.00 |  |  | 6.00 |  |
| Dicaprylyl carbonate |  | 3.00 |  |  |  |
| Cyclomethicone |  |  | 7.50 |  |  |
| Lanolin |  |  |  | 0.35 |  |
| PVP hexadecene copolymer | 0.50 |  |  | 0.50 | 1.00 |
| Ethylhexyloxyglycerol |  | 0.50 | 1.00 |  | 0.50 |
| Glycerol | 3.00 | 7.50 |  | 7.50 | 2.50 |
| Glycine soya |  | 1.50 | 1.00 |  |  |
| Vitamin E acetate | 0.50 | 0.20 | 0.25 | 0.75 | 1.00 |
| α-Glycosylrutin |  | 0.30 |  | 0.25 |  |
| Trisodium EDTA |  | 0.30 | 0.10 | 0.20 |  |
| Konkaben LMB ® | 0.20 |  |  |  | 0.15 |
| Methylparaben | 0.50 |  |  | 0.15 |  |
| Phenoxyethanol | 0.50 |  |  | 1.00 | 0.60 |
| Ethanol | 3.00 | 7.00 | 3.50 |  | 1.00 |
| Perfume | 0.20 |  | 0.20 | 0.40 | 0.20 |
| Dyes, water-soluble |  |  | 0.02 |  |  |
| Water | ad 100 | ad 100 | ad 100 | ad 100 | ad 100 |

7. Solids-stabilized emulsions

|  | 1 | 2 | 3 | 4 | 5 |
|---|---|---|---|---|---|
| Mineral oil |  |  | 16.00 | 16.00 |  |
| Octyldodecanol | 9.00 | 9.00 | 5.00 |  |  |
| Caprylic/capric triglyceride | 9.00 | 9.00 | 6.00 |  |  |
| C12-15-alkyl benzoates |  |  |  | 5.00 | 8.00 |
| Butylene glycol dicaprylate/dicaprate |  |  |  |  | 8.00 |
| Dicaprylyl ether | 9.00 |  |  | 4.00 |  |
| Dicaprylyl carbonate |  | 9.00 |  |  |  |
| Hydroxyoctacosanyl hydroxystearate | 2.00 | 2.00 | 2.00 | 2.00 | 1.50 |
| Disteardimonium hectorite | 1.00 | 0.750 | 0.50 | 0.50 | 0.25 |
| *Cera Microcristallina* + Paraffinum Liquidum |  |  | 2.50 |  | 5.00 |
| Hydroxypropylmethylcellulose | 0.15 |  |  |  | 0.05 |
| Dimethicone |  |  | 4.50 |  |  |
| UVASorb ® K2A | 2.00 | 5.00 | 3.00 | 1.50 | 1.00 |
| Uvinul ® A Plus | 1.00 | 0.25 | 2.75 | 1.00 | 0.50 |
| Bisethylhexyloxyphenyl methoxyphenyltriazine |  |  | 0.75 | 1.00 |  |
| Phenylbenzimidazolesulfonic acid | 2.00 | 0.50 |  |  |  |
| Ethylhexyl methoxycinnamate | 6.00 |  |  |  | 3.0 |
| Octocrylene | 3.50 |  | 7.50 |  |  |

7. Solids-stabilized emulsions

| | 1 | 2 | 3 | 4 | 5 |
|---|---|---|---|---|---|
| Ethylhexyl salicylate | | 3.50 | | | 4.00 |
| Diethylhexylbutamidotriazone | | | | | 4.0 |
| Titanium dioxide Eusolex ® T-2000 | | 2.00 | 4.00 | 2.00 | 4.00 |
| Silica dimethyl silylate | | | 1.00 | | |
| Boron nitride | 4.00 | | | 3.00 | |
| Tapioca starch | | | | 1.00 | |
| Sodium chloride | 1.00 | 1.00 | 1.00 | 1.00 | |
| Glycerol | 5.0 | 10.0 | | 6.00 | 10.0 |
| Trisodium EDTA | | | 1.00 | 1.00 | |
| Methylparaben | 0.21 | | | | 0.20 |
| Propylparaben | 0.07 | | | | |
| Phenoxyethanol | 0.50 | | 0.40 | 0.40 | 0.50 |
| Hexamidine diisethionate | | | | | 0.08 |
| Diazolidinylurea | | | 0.28 | 0.28 | |
| Alcohol | | 5.00 | | 2.50 | |
| Perfume | 0.45 | 0.20 | | | 0.45 |
| Water | ad 100 | ad 100 | ad 100 | ad 100 | ad 100 |

8. Oils and oil gels

| | 1 | 2 | 3 | 4 | 5 |
|---|---|---|---|---|---|
| Octyldodecanol | 9.00 | 9.00 | | | |
| Caprylic/capric triglyceride | 9.00 | | 6.00 | | |
| C12-15-alkyl benzoates | | | | 5.00 | 8.00 |
| Butylene glycol dicaprylate/dicaprate | | 9.00 | | | 8.00 |
| Dicaprylyl ether | 9.00 | | | 4.00 | |
| Dicaprylyl carbonate | | 7.00 | | | |
| Ethyl galactomannan (N-Hance ® AG 200) | 3.50 | | | | 4.00 |
| C20-40 fatty acids + polyethylenes (Performacid ®350) | | | | 3.60 | |
| Hydroxyoctacosanyl hydroxystearate | 2.00 | | | | |
| Disteardimonium hectorite | 1.00 | | | | 1.00 |
| Cetyl dimethicone | 0.50 | | 4.50 | | |
| Cyclomethicones | | | 15.00 | | 5.00 |
| UVASorb ® K2A | 2.00 | 5.00 | 3.00 | 1.50 | 1.00 |
| Uvinul A ® Plus | 1.00 | 3.50 | 2.75 | 2.00 | 0.50 |
| Ethylhexyl methoxycinnamate | 6.00 | | | 10.00 | 3.0 |
| Octocrylene | 3.50 | | 7.50 | 10.00 | |
| Ethylhexyl salicylate | | 3.50 | | | 4.00 |
| Ethylhexyltriazone | | | 2.00 | | |
| Diethylhexylbutamidotriazone | | 0.50 | | 3.00 | 4.0 |
| Phenoxyethanol | 0.50 | | | | |
| Perfume | 0.45 | 0.20 | | 0.45 | 0.45 |
| Dyes, oil-soluble | | | | 0.015 | 0.025 |
| Mineral oil | ad 100 | ad 100 | ad 100 | | |
| Rice oil | | | | ad 100 | ad 100 |

9. Sunscreen sticks (for lips and/or face)

| | 1 | 2 | 3 | 4 |
|---|---|---|---|---|
| Caprylic/capric triglyceride | 12.00 | 10 | 6 | |
| Octyldodecanol | 7.00 | 14 | 8 | 3 |
| Butylene glycol dicaprylate/dicaprate | | | | 12 |
| Pentaerythrityl tetraisostearate | 10.00 | 6 | 8 | 7 |
| Polyglyceryl-3 diisostearate | 2.50 | | | |
| Bisdiglyceryl polyacyl adipate-2 | 9.00 | 8.00 | 10.00 | 8.00 |
| Cetearyl alcohol | 8.00 | 11.00 | 9.00 | 7.00 |
| Myristyl myristate | 3.50 | 3.00 | 4.00 | 3.00 |
| Beeswax | 5.00 | 5.00 | 6.00 | 6.00 |
| *Cera carnauba* | 1.50 | 2.00 | 2.00 | 1.50 |
| *Cera Alba* | 0.50 | 0.50 | | 0.50 |
| C16-40-alkyl stearates | | 2.50 | 1.50 | 1.50 |
| UVASorb ® K2A | 2.00 | 4.50 | 3.00 | 0.50 |
| Uvinul A ® Plus | 3.00 | 1.00 | 0.50 | 1.00 |
| Bisethylhexyloxyphenyl methoxyphenyltriazine | 2.50 | | | 1.00 |
| Ethylhexyltriazone | 2.00 | | | |
| Diethylhexylbutamidotriazone | | | | 3.00 |
| Drometrizole trisiloxane | 1.00 | | 4.00 | |

-continued

9. Sunscreen sticks (for lips and/or face)

|  | 1 | 2 | 3 | 4 |
|---|---|---|---|---|
| Butylmethoxydibenzoylmethane |  | 1.00 | 1.00 |  |
| Z-Cote ® HP1 |  |  |  | 4.50 |
| MT-100 TV |  | 4.00 | 2.50 |  |
| Titanium dioxide T 805 |  | 3.60 |  | 5.00 |
| Ethylhexyl methoxycinnamate | 3.00 | 3.60 |  | 2.50 |
| Octocrylene |  |  | 7.50 |  |
| Benzophenone-3 |  |  | 3.50 |  |
| Tocopheryl acetate | 0.50 | 1.00 |  |  |
| Ascorbyl palmitate | 0.05 |  | 0.05 |  |
| *Buxus Chinensis* | 2.00 | 1.00 |  | 1.00 |
| Perfume, BHT | 0.10 | 0.25 |  | 0.35 |
| *Ricinus Communis* | ad 100 | ad 100 | ad 100 | ad 100 |

The invention claimed is:

1. A light-protective cosmetic or dermatological preparation, wherein the preparation comprises (a) at least one hydroxybenzophenone and (b) at least one benzoxazole derivative.

2. The preparation of in claim 1, wherein the at least one hydroxybenzophenone comprises at least one compound selected from compounds of general formula

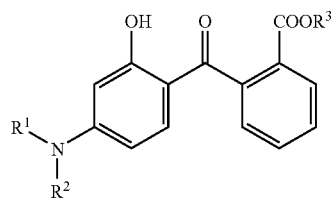

wherein $R^3$ represents a $C_1$-$C_{20}$ alkyl radical and wherein $R^1$ and $R^2$ independently represent hydrogen, $C_1$-$C_{20}$ alkyl, $C_3$-$C_{10}$ cycloalkyl or $C_3$-$C_{10}$ cycloalkenyl, or $R^1$ and $R^2$ together with the N atom to which they are linked form a 5-membered or 6-membered ring.

3. The preparation of claim 2, wherein the at least one hydroxybenzophenone comprises hexyl 2-(4'-diethylamino-2'-hydroxybenzoyl)benzoate.

4. The preparation of claim 1, wherein the at least one benzoxazole derivative comprises at least one compound of general formula

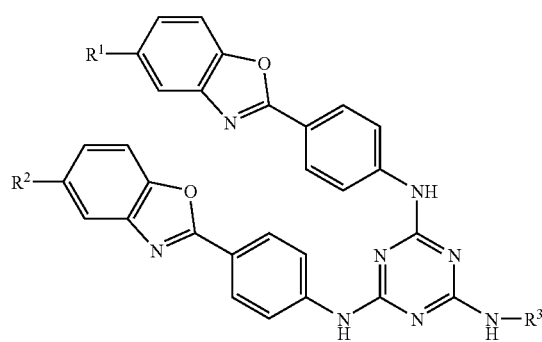

wherein $R^1$, $R^2$ and $R^3$ independently represent branched or unbranched, saturated or unsaturated alkyl radicals having from 1 to 10 carbon atoms.

5. The preparation of claim 4, wherein $R^1$ and $R^2$ both represent branched alkyl radicals having from 3 to 5 carbon atoms.

6. The preparation of claim 5, wherein $R^3$ represents a branched alkyl radical having 8 carbon atoms.

7. The preparation of claim 4, wherein the at least one benzoxazole derivative comprises 2,4-bis[5-1-(dimethylpropyl)benzoxazole-2-yl-(4-phenyl)imino]-6-(2-ethylhexyl)imino-1,3,5-triazine.

8. The preparation of claim 1, wherein a ratio (a):(b) is from 5:1 to 1:5.

9. The preparation of claim 1, wherein the preparation comprises at least one further UV filter substance.

10. The preparation of claim 9, wherein the at least one further UV filter substance comprises at least one substance selected from triazines, camphor derivatives, water-soluble UV filter substances, organic pigments and inorganic pigments.

11. The preparation of claim 9, wherein the at least one further UV filter substance comprises at least one UV filter substance that is liquid at room temperature.

12. The preparation of claim 9, wherein the at least one further UV filter substance comprises at least one substance selected from dibenzoylmethane derivatives, phenylene-1,4-bis(2-benzimidazyl)-3,3'-5,5'-tetrasulfonic acid bis-sodium salt, and 2,4-bis{[4-(2-ethylhexyloxy)-2-hydroxy]phenyl}-6-(4-methoxyphenyl)-1,3,5-triazine.

13. The preparation of claim 12, wherein the at least one further UV filter substance comprises 4-(tert-butyl)-4'-methoxydibenzoylmethane.

14. The preparation of claim 1, wherein the preparation is oil-free.

15. The preparation of claim 1, wherein the preparation further comprises at least one flavone glycoside.

16. The preparation of claim 15, wherein the at least one flavone glycoside comprises alpha-glucosylrutin.

17. The preparation of claim 1, wherein the preparation further comprises at least one active ingredient selected from 8-hexadecene-1,16-dicarboxylic acid and alpha-lipoic acid.

18. The preparation of claim 1, wherein the preparation further comprises at least one self-tanning substance.

19. The preparation of claim 18, wherein the at least one self-tanning substance comprises dihydroxyacetone.

20. The preparation of claim 1, wherein the preparation is free of ethylhexyl 2-cyano-3,3-diphenyl-acrylate.

21. The preparation of claim 1, wherein the preparation further comprises at least one insect repellent.

22. The preparation of claim 21, wherein the at least one insect repellent comprises ethyl 3-(N-n-butyl-N-acetylamino)propionate.

23. A method of protecting skin against light-induced skin aging, wherein the method comprises applying to the skin a preparation comprising (a) at least one hydroxybenzophenone and (b) at least one benzoxazole derivative.

24. The method of claim 23, wherein the at least one hydroxybenzophenone comprises at least one compound selected from compounds of general formula

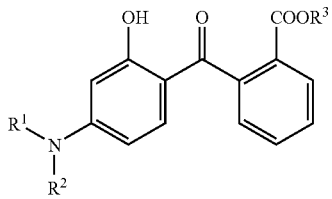

wherein $R^3$ represents a $C_1$-$C_{20}$ alkyl radical and wherein $R^1$ and $R^2$ independently represent hydrogen, $C_1$-$C_{20}$ alkyl, $C_3$-$C_{10}$ cycloalkyl or $C_3$-$C_{10}$ cycloalkenyl, or $R^1$ and $R^2$ together with the N atom to which they are linked form a 5-membered or 6-membered ring.

25. The method of claim 23, wherein the at least one hydroxybenzophenone comprises hexyl 2-(4'-diethylamino-2'-hydroxybenzoyl)benzoate.

26. The method of claim 23, wherein the at least one benzoxazole derivative comprises at least one compound of general formula

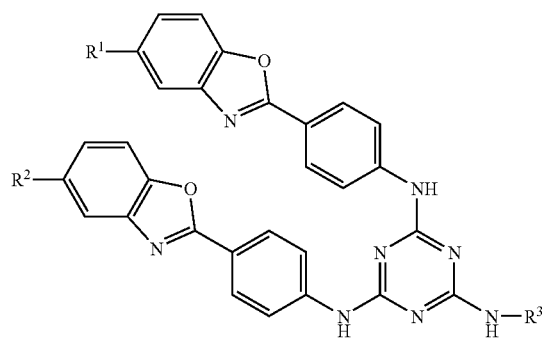

wherein $R^1$, $R^2$ and $R^3$ independently represent branched or unbranched, saturated or unsaturated alkyl radicals having from 1 to 10 carbon atoms.

27. The method of claim 26, wherein the at least one benzoxazole derivative comprises 2,4-bis[5-1-(dimethylpropyl)benzoxazole-2-yl-(4-phenyl)imino]-6-(2-ethyl-hexyl)imino-1,3,5-triazine.

28. The method of claim 23, wherein the preparation comprises at least one further UV filter substance selected from triazines, camphor derivatives, water-soluble UV filter substances, organic pigments and inorganic pigments.

29. The method of claim 23, wherein the preparation further comprises at least one UV filter substance that is liquid at room temperature.

30. The method of claim 23, wherein the preparation comprises at least one further UV filter substance selected from dibenzoylmethane derivatives, phenylene-1,4-bis(2-benzimidazyl)-3,3'-5,5'-tetrasulfonic acid bis-sodium salt, and 2,4-bis{[4-(2-ethylhexyloxy)-2-hydroxy]phenyl}-6-(4-methoxyphenyl)-1,3,5-triazine.

31. The method of claim 30, wherein the at least one further UV filter substance comprises 4-(tert-butyl)-4'-methoxydibenzoylmethane.

32. The method of claim 23, wherein the preparation further comprises at least one flavone glycoside.

33. The method of claim 23, wherein the preparation is free of ethylhexyl 2-cyano-3,3-diphenyl-acrylate.

34. A method of treating or preventing cosmetic or dermatological changes in skin, wherein the method comprises applying to the skin a cosmetic or dermatological preparation which comprises (a) at least one hydroxybenzophenone and (b) at least one benzoxazole derivative.

35. The method of claim 34, wherein the at least one hydroxybenzophenone comprises at least one compound selected from compounds of general formula

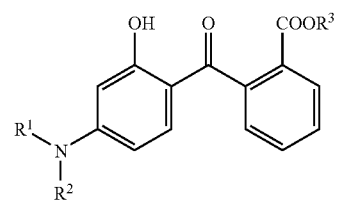

wherein $R^3$ represents a $C_1$-$C_{20}$ alkyl radical and wherein $R^1$ and $R^2$ independently represent hydrogen, $C_1$-$C_{20}$ alkyl, $C_3$-$C_{10}$ cycloalkyl or $C_3$-$C_{10}$ cycloalkenyl, or $R^1$ and $R^2$ together with the N atom to which they are linked form a 5-membered or 6-membered ring.

36. The method of claim 34, wherein the at least one hydroxybenzophenone comprises hexyl 2-(4'-diethylamino-2'-hydroxybenzoyl)benzoate.

37. The method of claim 35, wherein the at least one benzoxazole derivative comprises at least one compound of general formula

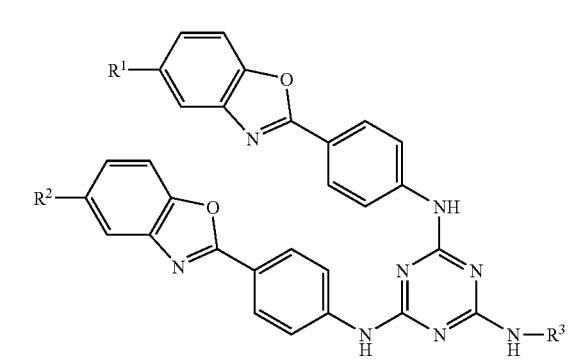

wherein $R^1$, $R^2$ and $R^3$ independently represent branched or unbranched, saturated or unsaturated alkyl radicals having from 1 to 10 carbon atoms.

38. The method of claim 37, wherein the at least one benzoxazole derivative comprises 2,4-bis[5-1-(dimethylpropyl)benzoxazole-2-yl-(4-phenyl)imino]-6-(2-ethyl-hexyl)imino-1,3,5-triazine.

39. A method of tanning or accelerating tanning of skin, wherein the method comprises applying to the skin a cosmetic or dermatological preparation which comprises (a) at least one hydroxybenzophenone and (b) at least one benzoxazole derivative.

40. The method of claim 39, wherein the at least one hydroxybeuzophenone comprises at least one compound selected from compounds of general formula

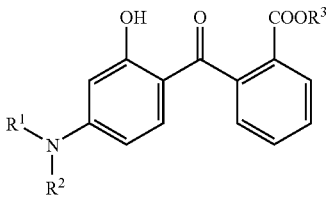

wherein $R^3$ represents a $C_1$-$C_{20}$ alkyl radical and wherein $R^1$ and $R^2$ independently represent hydrogen, $C_1$-$C_{20}$ alkyl, $C_3$-$C_{10}$ cycloalkyl or $C_3$-$C_{10}$ cycloalkenyl, or $R^1$ and $R^2$ together with the N atom to which they are linked form a 5-membered or 6-membered ring.

41. The method of claim 40, wherein the at least one hydroxybenzophenone comprises hexyl 2-(4'-diethylamino-2'-hydroxybenzoyl)benzoate.

42. The method of claim 39, wherein the at least one benzoxazole derivative comprises at least one compound of general formula

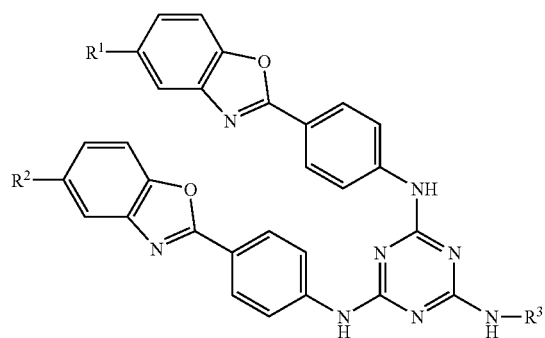

wherein $R^1$, $R^2$ and $R^3$ independently represent branched or unbranched, saturated or unsaturated alkyl radicals having from 1 to 10 carbon atoms.

43. The method of claim 42, wherein the at least one benzoxazole derivative comprises 2,4-bis[5-1-(dimethylpropyl)benzoxazole-2-yl-(4-phenyl)imino]-6-(2-ethyl-hexyl)imino-1,3,5-triazine.

44. The method of claim 42, wherein the preparation further comprises at least one self-tanning substance.

45. The method of claim 44, wherein the at least one self-tanning substance comprises dihydroxyacetone.

46. A cosmetic or dermatological wipe, wherein the wipe comprises a water-insoluble substrate that is impregnated with a preparation comprising (a) at least one hydroxybenzophenone and (b) at least one benzoxazole derivative.

47. The wipe of claim 46, wherein the at least one hydroxybenzophenone comprises at least one compound selected from compounds of general formula

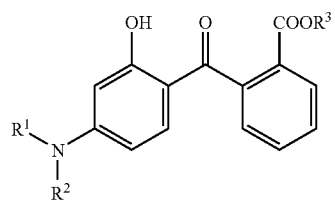

wherein $R^3$ represents a $C_1$-$C_{20}$ alkyl radical and wherein $R^1$ and $R^2$ independently represent hydrogen, $C_1$-$C_{20}$ alkyl, $C_3$-$C_{10}$ cycloalkyl or $C_3$-$C_{10}$ cycloalkenyl, or $R^1$ and $R^2$ together with the N atom to which they are linked form a 5-membered or 6-membered ring.

48. The wipe of claim 47, wherein the at least one hydroxybenzophenone comprises hexyl 2-(4'-diethylamino-2'-hydroxybenzoyl)benzoate.

49. The wipe of claim 46, wherein the at least one benzoxazole derivative comprises at least one compound of general formula

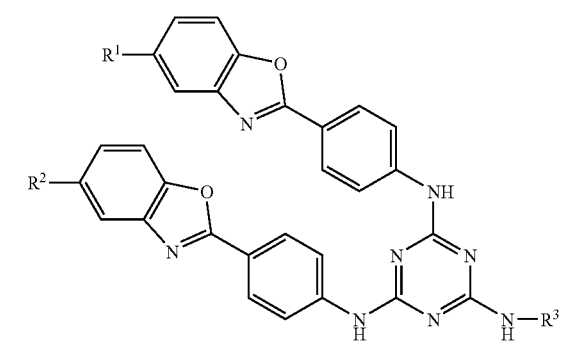

wherein $R^1$, $R^2$ and $R^3$ independently represent branched or unbranched, saturated or unsaturated alkyl radicals having from 1 to 10 carbon atoms.

50. The wipe of claim 49, wherein the at least one benzoxazole derivative comprises 2,4-bis[5-1-(dimethylpropyl)benzoxazole-2-yl-(4-phenyl)imino]-6-(2-ethyl-hexyl)imino-1,3,5-triazine.

* * * * *